(12) United States Patent
Chen et al.

(10) Patent No.: US 10,759,757 B2
(45) Date of Patent: Sep. 1, 2020

(54) CRYSTALLINE CONTRAST AGENT FOR MAGNETIC RESONANCE IMAGING, KIT AND COMPOSITION COMPRISING IT AND THEIR USE

(71) Applicants: Southern Medical University, Guangzhou (CN); Macau University of Science and Technology, Taipa (MO)

(72) Inventors: Jinxiang Chen, Taipa (MO); Jianxin Pang, Taipa (MO); Shuwen Liu, Taipa (MO); Li-Ping Bai, Taipa (MO); Zhi-Hong Jiang, Taipa (MO)

(73) Assignees: Macau University of Science and Technology, Tapa (MO); Southern Medical University, Guangzhou (CN)

( * ) Notice: Subject to any disclaimer, the term of this patent is extended or adjusted under 35 U.S.C. 154(b) by 220 days.

(21) Appl. No.: 15/271,368

(22) Filed: Sep. 21, 2016

(65) Prior Publication Data

US 2018/0078660 A1 Mar. 22, 2018

(51) Int. Cl.
*C07D 213/80* (2006.01)
*A61K 49/10* (2006.01)
*A61K 49/18* (2006.01)

(52) U.S. Cl.
CPC .......... *C07D 213/80* (2013.01); *A61K 49/103* (2013.01); *A61K 49/1818* (2013.01); *C07B 2200/13* (2013.01)

(58) Field of Classification Search
CPC ............................ A61K 49/106; C07D 213/80
See application file for complete search history.

(56) References Cited

FOREIGN PATENT DOCUMENTS

CN 20150952885 * 12/2015

OTHER PUBLICATIONS

Marie Kueny-stotz et al. Manganese-Enhanced MRI Contrast Agents: From Small Chelates to Nanosized Hybrids, Euro. J. Inorg. Chem., 1987-2005. (Year: 2012).*
Agnieszka Jablonska-Wawryycka et al. (Thermal behavior of manganese (II) complexes with pyridine-2,3-dicarbosylic acid, J. Therm. Anal Calorim, 110, 1367-1376. (Year: 2012).*
Zhang Chun-Xia et al. Synthesis and Crystal Structure of a New Three-dimensional Coordination Polymer: [Mn(2,3-pdc) (H 20)]0 (2,3-pdc = Pyridine-2,3-dicarboxylate), Chinese J. Struct. Chem, vol. 27(11), 1370-1374. (Year: 2008).*
J. Rimola, et al., "Non-invasive diagnosis of hepatocellular carcinoma < 2 cm in cirrhosis. Diagnostic accuracy assessing fat, capsule and signal intensity at dynamic MRI", J. Hepatol, 56(2012) 1317-1323.

A. Pohlmann, et al., "Linking non-invasive parametric MRI with invasive physiological measurements (MR-Physiol): towards a hybrid and integrated approach for investigation of acute kidney injury in rats", Acta Physiol. 207 (2013) 673-689.
D.L. Thorek, et al., "Non-invasive mapping of deep-tissue lymph nodes in live animals using a multimodal PET/MRI nanoparticle", Nat. Commun. 5(2014) 3097.
M. Cutajar, et al., "Comparison of ASL and DCE MRI for the non-invasive measurement of renal blood flow: quantification and reproducibility", Eur. Radiol. 24(2014) 1300-1308.
O. Bruder, et al., "2015 update on acute adverse reactions to gadolinium based contrast agents in cardiovascular MR. Large multi-national and multi-ethnical population experience with 37788 patients from the EuroCMR registry", J. Cardiov. Magn. Reson. 17(2015) 58.
E. Nance, et al., "Non-invasive delivery of stealth, brain-penetrating nanoparticles across the blood-brain barrier using MRI-guided focused ultrasound", J. Control Release 189(2014) 123-132.
J.M. Padowski, et al., "Neurochemical correlates of caudate atrophy in Huntington's disease", Mov. Disord. 29(2014) 327-335.
D.C. Alsop, et al., "Recommended implementation of arterial spin-labeled perfusion MRI for clinical applications: a consensus of the ISMRM perfusion study group and the European consortium for ASL in dementia", Magn. Reson. Med. 73(2015) 102-116.
B. Leporq et al., "Quantification of the triglyceride fatty acid composition with 3.0 T MRI", NMR Biomed. 27(2014) 1211-1221.
D. Lawson, et al., "Optimizing the high-field relaxivity by self-assembling of macrocyclic Gd(III) complexes", Dalton Trans. 44(2015) 4910-4917.
A.T. Preslar, et al., "Gd(III)-labeled peptide nanofibers for reporting on biomaterial localization in vivo", ACS Nano 8 (2014) 7325-7332.
S.Y. Yeo, et al., "Temperature-sensitive paramagnetic liposomes for image-guided drug delivery: Mn2+ versus [Gd (HPDO3A)(H2O)]", Biochim. Biophys. Acta 1838(2014) 2807-2816.

(Continued)

*Primary Examiner* — Michael G. Hartley
*Assistant Examiner* — Jagadishwar R Samala
(74) *Attorney, Agent, or Firm* — Renner Kenner Greive Bobak Taylor & Weber

(57) ABSTRACT

A method of preparing a crystalline contrast agent for magnetic resonance imaging from a zwitterionic carboxylic pyridyl ligand includes mixing metal ion and the pyridyl ligand and obtaining crystals therefrom. The crystalline contrast agent includes a manganese-organic or gadolinium-organic 3D framework. The crystalline contrast agent is employed in a kit and a pharmaceutically acceptable composition. The method allows for preparing crystalline contrast agents with superior properties with easily available starting materials and with an economic and efficient process. The method allows for preparing crystalline contrast agents with exceptional water-stability and water-solubility, which exhibit high longitudinal relaxivities and with excellent stabilities under physiological conditions and low cytotoxicity. Further provided is a method for in vivo imaging of a subject, in particular a human, comprising administering the crystalline contrast agent to the subject.

7 Claims, 24 Drawing Sheets
(13 of 24 Drawing Sheet(s) Filed in Color)

(56) References Cited

OTHER PUBLICATIONS

R. Artali, et al., "Solution thermodynamics, computational and relaxometric studies of ditopic DO3A-based Mn (ii) complexes", New. J. Chem. 39(2015) 539-547.
A.J. Villaraza, et al., "Macromolecules, dendrimers, and nanomaterials in magnetic resonance imaging: the interplay between size, function, and pharmacokinetics", Chem. Rev. 110(2010) 2921-2959.
M.W. Rotz, et al., "High relaxivity Gd(III)-DNA gold nanostars: investigation of shape effects on proton relaxation", ACS Nano 9(2015) 3385-3396.
J. Della Rocca, "Nanoscale metal-organic frameworks: magnetic resonance imaging contrast agents and beyond", Eur. J. Inorg. Chem. 24(2010) 3725-3734.
J. Della Rocca, et al., "Nanoscale metal-organic frameworks for biomedical imaging and drug delivery", Acc. Chem. Res. 44(2011) 957-968.
C. Wang, et al., "Metal-organic frameworks as a tunable platform for designing functional molecular materials", J. Am. Chem. Soc. 135(2013) 13222-13234.
D. Liu, et al., "Metal-organic frameworks as sensory materials and imaging agents", Inorg. Chem. 53(2014) 1916-1924.
C. Pei, et al., "Synthesis of copolymerized porous organic frameworks with high gas storage capabilities at both high and low pressures", Chem. Commun. 50(2014) 6134-6136.
Y.S. Bae, et al., "The effect of pyridine modificaiton of Ni-DOBDC on CO2 capture under humid conditions", Chem. Commun. 50(2014) 3296-3298.
A.M. Fracaroli, et al., "Metal-organic frameworks with precisely designed interior for carbon dioxide capture in the presence of water", J. Am. Chem. Soc. 13(2014) 8863-8866.
J.A. Brant, et al., "Li2CdGeS4, a diamond-like semiconductor with strong second-order optical nonlinearity in the infrared and exceptional laser damage threshold", Chem. Mater. 26(2014) 3045-3048.
L.N. Duan, et al., "An interpenetrated bioactive nonlinear optical MOF containing a coordinated quinolone-like drug and Zn (ii) for pH-responsive release", Dalton Trans. 44(2015) 1800-1804.
H.G.T. Nguyen, et al., "Vanadium-node-functionalized UiO-66: a thermally stable MOF-supported catalyst for the gas-phase oxidative dehydrogenation of cyclohexene", ACS Catal. 4(2014) 2496-2500.
K. Mo, et al., "A homochiral metal-organic framework as an effective asymmetric catalyst for cyanohydrin synthesis", J. Am. Chem. Soc. 136(2014) 1746-1749.
D.W. Ryu, et al., "Two homochiral bimetallic metal-organic frameworks composed of a paramagnetic metalloligand and chiral camphorates: multifunctional properties of sorption, magnetism, and enantioselective separation", Cryst. Growth Des. 14(2014) 6472-6477.
R.A. Agarwal, et al., "Gas Adsorption, Magnetism, and Single-Crystal to Single-Crystal Transformation Studies of a Three-Dimensional Mn(II) Porous Coordination Polymer", Cryst. Growth Des. 14(2014) 5585-5592.

S. Bhattacharyya, et al., "A bimodal anionic MOF: turn-off sensing of CuII and specific sensitization of EuIII", Chem. Commun. 50(2014) 13567-13570.
B.Y.W. Man, et al., "Group 9 metal-based inhibitors of B-amyloid (1-40) fibrillation as potential therapeutic agents for Alzheimer's disease", Chem. Sci. 2(2011) 917-921.
S.H. Chen, et al., "Development of a Gd (III)-based receptor-induced magnetization enhancement (RIME) contrast agent for B-glucuronidase activity profiling", Inorg. Chem. 51(2012) 12426-12435.
E. Molnar, et al., "Picolinate-containing macrocyclic Mn2+ complexes as potential MRI contrast agents", Inorg. Chem. 53(2014) 5136-5149.
J.A. Greathouse, et al., "The interaction of water with MOF-5 simulated by molecular dynamics", J. Am. Chem. Soc. 128(2006) 10678-10679.
J.X. Chen, et al., "Bent tritopic carboxylates for coordination networks: clues to the origin of self-penetration", CrystEngComm. 16(2014) 7722-7730.
L.Qin, et al., "A water-stable metal-organic framework of a zwitterionic carboxylate with dysprosium: a sensing platform for Ebolavirus RNA sequences", Chem. Commu. 52(2016) 132-135.
S.P. Yang, et al., "Platforms formed from a three-dimensional Cu-based zwitterionic metal-organic framework and probe ss-DNA: selective fluorescent biosensors for human immunodeficiency virus 1 ds-DNA and Sudan virus RNA sequences", Anal. Chem. 87(2015) 12206-12214.
P. Marckmann, et al., "Nephrogenic systemic fibrosis: suspected causative role of gadodiamide used for contrast- enhanced magnetic resonance imaging", J. Am Soc. Nephrol. 17(2006) 2359-2362.
C. Thakral, et al., "Long-term retention of gadolinium in tissues from nephrogenic systemic fibrosis patient after multiple gadolinium-enhanced MRI scans: case report and implications", Contrast Media Mol. Imaging 2(2007) 199-205.
M.A. Sieber, et al., "Gadolinium-based contrast agents and their potential role in the pathogenesis of nephrogenic systemic fibrosis: the role of excess ligand", Magn. Reson. Imaging 27(2008) 955-962.
T. Kundu, et al., "Mechanical downsizing of a gadolinium(III)-based metal-organic framework for anticancer drug delivery", Chemistry 20(2014) 10514-10518.
Y. Yan, et al. "Microwave-assisted synthesis of Gd (iii)-loaded nanozeolite SOD as MRI contrast agent with remarkable stability in vivo", J. Mater. Chem. B 2(2014) 3041-3049.
T.H. Shin, et al., "T1 and T2 dual-mode MRI contrast agent for enhancing accuracy by engineered nanomaterials", ACS Nano 8(2014) 3393-3401.
W.J. Rieter, et al., "Nanoscale metal-organic frameworks as potential multimodal contrast enhancing agents", J. Am. Chem. Soc. 128(2006) 9024-9025.
K.M. Taylor, et al., "Surfactant-assisted synthesis of nanoscale gadolinium metal-organic frameworks for potential multimodal imaging", Angew Chem. Int. Ed. Engl. 47(2008) 7722-7725.
K.M. Taylor, et al., "Mesoporous silica nanospheres as highly efficient MRI contrast agents", J. Am. Chem. Soc. 130 (2008) 2154-2155.

\* cited by examiner

CRYSTALLINE CONTRAST AGENT FOR MAGNETIC RESONANCE IMAGING, KIT AND COMPOSITION COMPRISING IT AND THEIR USE

FIELD OF THE INVENTION

The present invention relates to a method of preparing a crystalline contrast agent for magnetic resonance imaging from a zwitterionic pyridyl carbon/late ligand and the crystalline contrast agent obtained or obtainable with said method. The crystalline contrast agent in particular essentially consists of a manganese-organic or gadolinium-organic 3D framework. The present invention further provides a kit and a pharmaceutically acceptable composition comprising said crystalline contrast agent. Further provided is a method for in vivo imaging of a subject, in particular a human, comprising administering said crystalline contrast agent to the subject.

BACKGROUND OF THE INVENTION

Various imaging techniques including magnetic resonance imaging (MRI), computed tomography, positron emission tomography, and optical microscopy in the bioimaging fields have been employed for disease and other diagnosis. Among these imaging methods, MRI is known as a powerful medical diagnostic technique due to its inherent advantages such as non-invasiveness, safety, and high spatial resolution. It can differentiate abnormalities from normal tissues based on their varied NMR water proton signals arising from different water densities and/or nuclear relaxation rates. Compounds of highly paramagnetic metal ions, such as $Gd^{3+}$ and $Mn^{2+}$ are often administered to facilitate a more accurate diagnosis by enhancing the contrast between tissues by increasing water proton relaxation rates. Because $Gd^{3+}$ has high electron spin ($S=7/2$) and low electronic relaxation, Gd-based compounds, in particular Gd-DTPA (DTPA=diethylene triamine pentaacetic acid) have been clinically used as MRI positive contrast agents. However, the use of MRI agents of the Gd-DTPA type is limited due to their only moderate longitudinal ($r_1$) relaxation rates and a required large administration dose (several grams per patient). The latter is a serious concern for patients with severe kidney failure.

In this regard, metal-organic frameworks (MOFs) have recently emerged as MRI contrast agents and received increased attention as they allow for three-dimensional images with high spatial resolution (Della Rocca, J., Lin, W., Nanoscale metal-organic frameworks: magnetic resonance imaging contrast agents and beyond, Eur. J. Inorg. Chem. 24(2010) 3725-3734, Della Rocca, J. et al., Nanoscale metal-organic frameworks for biomedical imaging and drug delivery, Acc. Chem. Res. 44(2011) 957-968, Horcajada, P. et al., Metal-organic frameworks in biomedicine, Chem. Rev. 112(2012) 1232-1268, Wang, C. et al., Metal-organic frameworks as a tunable platform for designing functional molecular materials, J. Am. Chem. Soc. 135(2013) 13222-13234, Liu, D. et al., Metal-organic frameworks as sensory materials and imaging agents, Inorg. Chem. 53(2014) 1916-1924).

MOFs are a class of hybrid materials composed of metal ions connected by a variety of organic ligands through non-covalent bonds. They have shown high potential applicability in diverse fields, such as gas adsorption, storage and separation, nonlinear optics, catalysis, and biomedical applications. As MRI agents, MOFs have many advantages, in particular in carrying large amounts of paramagnetic metal ions. For example, $Gd^{3+}$ and $Mn^{2+}$ containing MOFs have shown excellent efficacy as $T_1$-weighted contrast agents with large per metal- and particle-based MRI relaxivity (Chen, S. H. et al., Development of a Gd (III)-based receptor-induced magnetization enhancement (RIME) contrast agent for δ-glucuronidase activity profiling, Inorg. Chem. 51(2012) 12426-12435, Molnar, E. et al., Picolinate-containing macrocyclic $Mn^{2+}$ complexes as potential MRI contrast agents, Inorg. Chem. 53(2014) 5136-5149). Recently, it is reported that $Mn^{2+}$ centers in MOFs exhibit very high in vivo $r_1$ MRI relaxivities by binding to intracellular proteins.

For future clinical application, moisture stability and water solubility are important prerequisites for MOFs to function in the basic in vivo environment. However, low moisture stability and water insolubility of many MOFs significantly limit their application (Greathouse, J. A., Allendorf, M. D., The interaction of water with MOF-5 simulated by molecular dynamics, J. Am. Chem. Soc. 128(2006) 10678-10679). Moreover, the cytotoxicity of some MOF backbones is an issue further limiting its theoretical clinical use (Kundu, T. et al., Mechanical downsizing of a gadolinium(III)-based metal-organic framework for anticancer drug delivery, Chemistry 20(2014) 10514-10518).

Accordingly, there remains a strong need for economic and cost-efficient manufacturing processes and obtainable compounds suitable as contrast agents for magnetic resonance imaging with sufficiently high longitudinal ($r_1$) relaxation rates under the administration of acceptable doses. Such compounds shall possess low cytotoxicity and need to have an appropriate moisture stability and water solubility as prerequisite for the in vivo utilization.

SUMMARY OF THE INVENTION

The first aspect of the present invention relates to a method of preparing a crystalline contrast agent for magnetic resonance imaging.

Namely the method of the present invention comprises steps of:
(i) preparing a mixture, in particular an aqueous solution, comprising a metal ion and a pyridyl ligand which pyridyl ligand is a zwitterionic pyridyl ligand having three carboxylic acid moieties;
(ii) subjecting the obtained mixture to conditions under which crystals of the contrast agent are formed;
(iii) separating the crystals of the contrast agent.

The pyridyl ligand in particular has a structure of Formula (I):

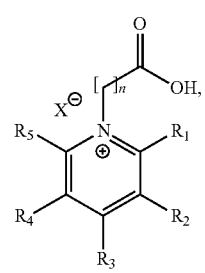

Formula (I)

wherein X is a halogen and selected from Br, Cl or I, n is an integer and selected from 0, 1, 2 or 3, and wherein two of $R^1$ to $R^5$ are a group of Formula (II)

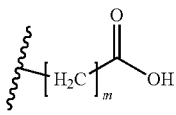

Formula (II)

with m being an integer and selected from 0, 1 or 2 and the other of $R^1$ to $R^5$ being hydrogen. In most preferred embodiments, the pyridyl ligand has a structure of Formula (III):

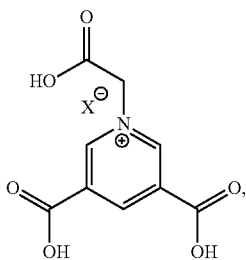

Formula (III)

wherein X is Br.

The metal ion is in particular selected from manganese with the oxidation state +2 or gadolinium with the oxidation state +3.

In another aspect, the present invention refers to a crystalline contrast agent obtained by the method described above. In particular, the crystalline contrast agent essentially consists of a manganese-organic compound comprising repeating coordination entities which can be described with the formula $\{[Mn_2(Cmdcp)_2(H_2O)_2](H_2O)\}$ extending in three dimensions (3D framework) or a gadolinium-organic compound comprising repeating coordination entities which can be described with the formula $\{[Gd(Cmdcp)(H_2O)_3](NO_3).3H_2O\}$ extending in three dimensions (3D framework).

Further provided by the present invention is a method for in vivo imaging of a subject, in particular a human. The method comprises:
(i) administering to the subject the crystalline contrast agent obtained or obtainable with the preparation method described above, in particular by oral or intravenous administration;
(ii) waiting a time sufficient to allow the contrast agent to accumulate at the site to be imaged; and
(iii) imaging the site to be imaged with magnetic resonance imaging for obtaining one or more magnetic resonance images. The site to be imaged in particular includes one or both kidneys.

The crystalline contrast agent most preferably essentially consists of a manganese-organic compound comprising repeating coordination entities which can be described with the formula $\{[Mn_2(Cmdcp)_2(H_2O)_2](H_2O)\}$ extending in three dimensions (3D framework).

The present invention further provides a kit or pharmaceutically acceptable composition comprising the contrast agent obtained or obtainable by the preparation method described above. Further provided is the use of the crystalline contrast agent, the kit or the pharmaceutically acceptable composition comprising said crystalline contrast agent for in vivo imaging of a subject by means of magnetic resonance imaging.

The preparation method of the present invention allows for preparing the crystalline contrast agents with superior properties with easily available starting materials and with an economic and efficient process which can be easily scaled-up. The obtained crystalline contrast agents have an exceptional water-stability and water-solubility and high $r_1$ relaxivities.

In particular, the preparation method of the present invention allows for preparing metal-organic frameworks, namely 3D manganese and gadolinium-organic frameworks including $\{[Mn_2(Cmdcp)_2(H_2O)_2](H_2O)\}_n$ (also referenced as compound 1, $H_3CmdcpBr=N$-(4-carboxy methyl)-(3,5-dicarboxyl)pyridinium bromide, also referred to as 3,5-dicarboxy-1-(carboxymethyl)pyridin-1-ium bromide) and $\{[Gd(Cmdcp)(H_2O)_3](NO_3).3H_2O\}_n$ (also referenced as compound 2). In vitro magnetic resonance imaging measurements confirmed that both compounds exhibit longitudinal relaxivities $r_1$ superior to that of the control Gd-DTPA and excellent stabilities under physiological conditions. Besides, both compounds proved to have particular biocompatibility and very low cytotoxicity. In vivo magnetic resonance imaging measurements further proved advantageously high resolution magnetic resonance imaging through a high contrast efficacy and a prolonged acquisition timeframe. The results confirm that in particular compound 1 and compound 2 are highly promising contrast agents for in vivo imaging of a variety of diseases and organs such as intravascular diseases and renal dysfunction—both compounds proved to be promising next-generation intravascular magnetic resonance imaging contrast agents for living subjects.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10B shows the $r_1$ relaxivity curves of compounds 1 (curve "1") and 2 (curve "2") and Gd-DTPA. The relaxivity rates of compounds 1 and 2 and Gd-DTPA are 17.90, 13.75 and 4.98 $mM^{-1}S^{-1}$, respectively.

DETAILED DESCRIPTION OF THE INVENTION

Figure 1A:
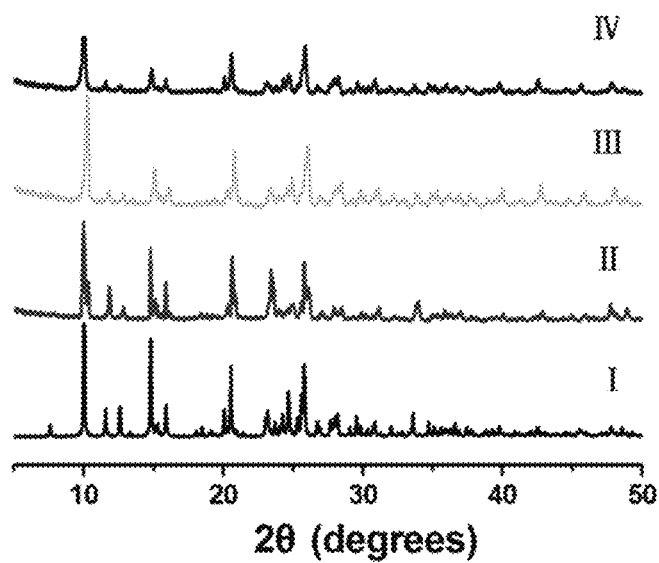
FIG. 1A shows powder X-ray diffraction patterns of $\{[Mn_2(Cmdcp)_2(H_2O)_2](H_2O)\}_n$ (compound 1) showing agreement between the simulated (I), synthesized (II), the fresh powder immersed in $H_2O$ for 24 h (III) and the fresh powder immersed in rats' serum for 24 h (IV).

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise. In particular the expression "a metal ion" and "a pyridyl ligand" as used in step (i) of the method for preparing the crystalline contrast agent shall mean a plurality of said metal ion and pyridyl ligand.

The present invention provides a method of preparing a crystalline contrast agent for magnetic resonance imaging.

Contrast agents are generally compounds which are able to alter the relaxation properties of tissues and induce an image contrast such as in magnetic resonance imaging. They are typically paramagnetic, superparamagnetic, or ferromagnetic. The extent to which a contrast agent can alter the relaxation rate is called its relaxivity which is defined as the difference in the relaxation rate of a sample measured with contrast agent and without the contrast agent. It is expressed as "$r_1$" or "$r_2$" which refers to the changes in longitudinal ($1/\Delta T_1$) and transverse ($1/\Delta T_2$) relaxation rate, respectively.

The contrast agent for magnetic resonance imaging prepared according to the method of the present invention comprises and in particular essentially consists of a metal-organic framework (MOF). MOFs are crystalline compounds composed of two major components: a metal ion or cluster of metal ions and an organic molecule as a ligand, as mono-, di-, tri- or polydentate ligand. The metal ion(s) are coordinated to the ligand to form one-, two- or three-dimensional structures formed by repeating coordination entities extending in one, two or three dimensions. The choice of metal(s) and ligands influences the structure and properties of the MOF such as the size and shape of pores.

The contrast agent prepared according to the method of the present invention is crystalline, which shall mean that the atoms or molecules are substantially organized in a structure known as a crystal. Said term is generally used in the art for any structure of ions, molecules, or atoms that are held together in an ordered arrangement. A crystalline structure is one of two types of structural ordering of atoms, ions or molecules the other being the amorphous structure which is irregular and lacks an orderly arrangement of structural units. Whether a compound is crystalline and the respective crystal system can, for example, be confirmed by means of X-ray diffraction. Preferably, the crystalline contrast agent crystallizes in a monoclinic space group.

The crystalline contrast agent is prepared from a zwitterionic pyridyl carboxylate ligand. More specifically, the method of preparing the crystalline contrast agent for magnetic resonance imaging comprises steps of:

(i) preparing a mixture comprising a metal ion and a pyridyl ligand which pyridyl ligand is a zwitterionic pyridyl ligand having three carboxylic acid moieties;

(ii) subjecting the obtained mixture to conditions under which crystals of the contrast agent are formed;

(iii) separating the crystals of the contrast agent.

The term "pyridyl ligand" as used herein generally refers to a ligand comprising at least one optionally substituted pyridine ring. The pyridyl ligand of step (i) is a pyridyl ligand which has three carboxylic acid moieties, which means herein three free carboxylic acid functions. Those three carboxylic acid moieties can be directly or indirectly attached to the at least one pyridine ring, wherein indirectly attached means that there are methylene groups in between the carboxylic acid moieties and the pyridine ring. The pyridyl ligand is zwitterionic, i.e. is a molecule with both positive and negative electrical charges. The pyridyl ligand preferably has a structure of Formula (I):

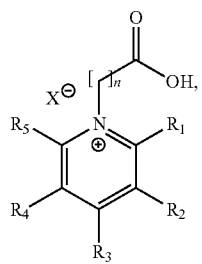

Formula (I)

wherein X is a halogen and preferably selected from Br, Cl or I. More preferably, X is Br. n is an integer and selected from 0, 1, 2 or 3, preferably from 1 or 2 and most preferably 1. Two of $R^1$ to $R^5$ are a group of Formula (II):

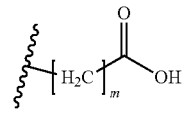

Formula (II)

with m being an integer and selected from 0, 1 or 2 and the other of $R^1$ to $R^5$ being hydrogen. m is more preferably 0 or 1, most preferably 0. In preferred embodiments of the present invention, $R_2$ and $R_4$ are a group of Formula (II) and are preferably directly attached to carbon atoms in the pyridine ring.

In particular embodiments of the present invention, the pyridyl ligand has a structure of Formula (III):

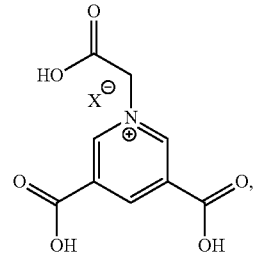

Formula (III)

with X being as defined above. More preferably, X is Br. Such pyridyl ligand can be prepared, for example, by the method described in Chen, J. X. et al. (Bent tritopic carboxylates for coordination networks: clues to the origin of self-penetration, Cryst Eng Comm. 16(2014) 7722-7730). The feature that the mixture comprises the pyridyl ligand as used herein is to be understood to cover any protonated or deprotonated form of said pyridyl ligand due to the presence of further components in the mixture added, for example, for dissolving it.

The metal ion is an ion of a metal suitable for magnetic resonance imaging namely those who are able in form of a respective metal-organic framework with the pyridyl ligand to shorten the relaxation times of atoms within body tissues following administration, in particular to shorten the $T_1$ relaxation time. Metal ions according to the present invention are in particular those with paramagnetic properties.

In particular, the metal ion is a divalent or trivalent metal ion. The metal ion is preferably selected from manganese ion or gadolinium ion. The manganese ion is in particular a manganese ion in the +2 oxidation state. The gadolinium ion is in particular in the +3 oxidation state. The metal ion is preferably provided in the form of a metal salt.

Step (i) of the method of the present invention preferably comprises steps of:

a) preparing a first pre-mixture comprising mixing the pyridyl ligand, a solvent and a base;

b) preparing a second pre-mixture comprising mixing a metal salt and a solvent; and c) adding the second pre-mixture to the first pre-mixture.

The solvent in step a) preferably comprises water, more preferably essentially consists of water. The base is preferably an alkali hydroxide. Alkali hydroxides are a class of chemical compounds which are composed of an alkali metal cation, i.e. one of lithium (Li), sodium (Na), potassium (K), rubidium (Rb), caesium (Cs), and the hydroxide anion (HO—). In particular, the alkali metal cation is K or Na.

More preferably, the base is NaOH, i.e. sodium hydroxide. In such embodiments, the first pre-mixture comprises the solvent of step a) and NaOH.

Step a) preferably comprises mixing the pyridyl ligand and the solvent and subsequently adjusting the pH of the mixture to a pH of between 5.5 and 7.5, more preferably to a pH of about 6.0 to 7.0, by adding the base. In embodiments in which the metal ion is a manganese ion, the pH is preferably adjusted to about 7.0 by adding the base. In embodiments in which the metal ion is a gadolinium ion, the pH is preferably adjusted to about 6.0 by adding the base.

The metal salt in step b) is a salt of the metal, preferably a nitrate, halogenid like chloride or bromide, sulfate, acetate, tartrate and the like of the metal. The metal salt of step b) is preferably a halogenid or a nitrate including hydrates. Preferably, the metal salt is selected from a hydrate of $Gd(NO_3)_3$, in particular the hexahydrate, or $MnCl_2$. Thus, the metal salt is most preferably selected from $Gd(NO_3)_3 \times 6\ H_2O$ or $MnCl_2$. The solvent in step b) preferably comprises and in particular essentially consists of water.

Most preferably, the solvent of step a) and the solvent of step b) comprise and in particular essentially consist of water.

Step (i) optionally comprises a further step d) of stirring the mixture obtained in step c) for between 30 min and 90 min, in particular for about 30 min preferably at a temperature of between 80° C. and 120° C., more preferably at about 100° C. and/or of filtering the optionally stirred mixture of step c). In embodiments of the present invention, the mixture obtained in step c) is stirred for between 30 min and 90 min, in particular for about 30 min, preferably at a temperature of between 80° C. and 120° C., more preferably at about 100° C., cooled down to a temperature of between 20° C. and 30° C., preferably to about 25±2° C., and then filtered, for obtaining the mixture of step (i) as the filtrate.

The mixture prepared in step (i) is preferably a solution, i.e. a homogeneous mixture comprising the metal ion and the pyridyl ligand in the solvents from step a) and b) and the base, in particular both solvents essentially consist of water and the base is NaOH. In particular, the first pre-mixture prepared in step a) is a dispersion or solution comprising the pyridyl ligand in water and NaOH and the second pre-mixture prepared in step b) is a solution comprising the metal salt in water.

The mixture in step (i) is preferably prepared by suspending or dissolving the pyridyl ligand in water and adjusting the pH to about 5.5 to 7.5 by means of NaOH, preparing a solution of the metal salt in water and adding said solution to the solution or dispersion comprising the pyridyl ligand.

The pyridyl ligand and the metal salt are preferably used for preparing the mixture of step (i), in particular solution, in a molar ratio of the pyridyl ligand to the metal salt of between 0.8:1 and 1.8:1, in particular about 1:1 to about 1.5:1.

Step (ii) of the method of the present invention preferably comprises steps of:
a) optionally stirring the mixture of step (i); and
b) subjecting the mixture of step (i) to a temperature of between 20° C. and 30° C. for at least 48 hours for forming crystals of the contrast agent.

Step b) of step (ii) in particular comprises and is more preferably is carried out by means of allowing the mixture to stand at a temperature between 20° C. and 30° C. for at least 48 hours for forming crystals of the contrast agent. The temperature is preferably 25±2° C. Preferably, the mixture is allowed to stand at a temperature between 20° C. and 30° C., preferably at 25±2° C., for more than 48 hours for forming crystals of the contrast agent.

Step (iii) of the method of the present invention preferably comprises steps of:
a) separating the crystals from the mixture, preferably separating the crystals from the mixture by filtration and optionally further purifying the crystals such as by washing with a washing solvent;
b) drying the crystals, preferably by vacuum drying.

In an embodiment of the present invention, the crystalline contrast agent essentially consists of a crystalline manganese-organic compound and the method comprises steps of:
(i) preparing a mixture comprising a manganese ion and the pyridyl ligand of Formula (III) with X being Br which step (i) comprises steps of:
   a) preparing a first pre-mixture comprising mixing the pyridyl ligand and water and adjusting the pH to a pH of about 7.0 by adding sodium hydroxide, preferably suspending the pyridyl ligand in water and adjusting the pH with sodium hydroxide such as 0.1 M sodium hydroxide to a pH of about 7.0,
   b) preparing a second pre-mixture comprising mixing $MnCl_2$ and water;
   c) adding the second pre-mixture to the first pre-mixture;
   d) stirring the mixture obtained in step c) for between 30 min and 90 min at a temperature of between 80° C. and 120° C., cooling the mixture down to a temperature of between 20° C. and 30° C. and filtering for obtaining the mixture of step (i) as filtrate. In particular, the mixture is stirred for about 30 min at a temperature of about 100° C. and cooled down to a temperature of about 25±2° C., such as by allowing the stirred mixture to stand at a temperature of about 25±2° C. and is then filtered.
(ii) allowing the mixture to stand at a temperature between 20° C. and 30° C. for at least 48 hours for forming crystals of the manganese-organic compound. The temperature is preferably about 25±2° C. Preferably, the mixture is allowed to stand at a temperature between 20° C. and 30° C., in particular at about 25±2° C., for more than 48 hours for forming the crystals.
(iii) separating the crystals of the manganese-organic compound by filtration and then drying the crystals.

In another embodiment of the present invention, the crystalline contrast agent essentially consists of a crystalline gadolinium-organic compound and the method comprises steps of:
(i) preparing a mixture comprising a gadolinium ion and the pyridyl ligand of Formula (III) with X being Br, which step (i) comprises steps of:
   a) preparing a first pre-mixture comprising mixing the pyridyl ligand and water and adjusting the pH to a pH of about 6.0 by adding sodium hydroxide such as 0.1 M sodium hydroxide;
   b) preparing a second pre-mixture comprising mixing $Gd(NO_3)_3 \times 6\ H_2O$ and water;
   c) adding the second pre-mixture to the first pre-mixture;
(ii) stirring the mixture of step (i) for between 30 min and 90 min at a temperature of between 20° C. and 30° C. and allowing the mixture after the stirring to stand at a temperature between 20° C. and 30° C. for at least 48 hours for forming crystals of the gadolinium-organic compound. The temperature is preferably about 5±2° C. Preferably, the mixture is allowed to stand at a temperature between 20° C. and 30° C., in particular at about 25±2° C., for more than 48 hours for forming the crystals.

(iii) separating the crystals of the gadolinium-organic compound by filtration and then drying the crystals.

The present invention refers in a second aspect to the crystalline contrast agent obtained or obtainable by the method described above. In one embodiment, a crystalline contrast agent is provided obtained by the method described above. In another embodiment, a crystalline contrast agent is provided obtainable by the method described above.

The crystalline contrast agent preferably has a molar water solubility of at least 0.1 µM at a temperature of about 25±2° C. More preferably, the molar water solubility is at least about 0.5 µM and in particular embodiments at least about 1 mM.

The crystalline contrast agent preferably exhibits a longitudinal relaxivity $r_1$ of greater than 5 mM$^{-1}$s$^{-1}$ calculated based on the molecular concentration of the contrast agent. In more preferred embodiments, the contrast agent exhibits a longitudinal relaxivity $r_1$ of greater than 8 mM$^{-1}$s$^{-1}$, or greater than 10 mM$^{-1}$s$^{-1}$ or greater than 15 mM$^{-1}$s$^{-1}$ calculated based on the molecular concentration of the contrast agent in particular when applying a common magnetic field strengths ranging from 1.5 to 7 T (kg·s$^{-2}$·A$^{-1}$) such as of 3.0 T or 7.0 T. The relaxivity $r_1$ as used herein refers to the value determined at about 30° C. in deionized water. The crystalline contrast agent obtained or obtainable with the method described above is preferably stable up to 250° C. and more preferably up to 300° C. which can be confirmed by means of thermogravimetric analysis (TGA).

The metal ion release from the crystalline contrast agent is preferably less than 10 mol %, in particular less than 5 mol % after dissolving the crystalline contrast agent in water at ambient conditions such as at 25±2° C. for about 48 h.

The crystalline contrast agent preferably comprises nanocrystals, i.e. crystals with an average diameter below 1000 nm. More preferably, the crystalline contrast agent preferably comprises crystals with an average diameter of less than about 100 nm, more preferably of less than about 90 nm. "Diameter" as used herein preferably refers to the Feret (or Feret's) diameter at the thickest point of a crystal. The Feret diameter is a measure of an object size along a specified direction and can be defined as the distance between the two parallel planes restricting the object perpendicular to that direction. I.e. if the Feret diameters measured for different directions differ, the "diameter" referred to in the present patent application always refers to the highest value measured. "Average diameter" refers to the average of "diameter" preferably measured with at least 10 crystals. The diameter is preferably measured by means of Transmission electron microscopy (TEM).

In a preferred embodiment of the present invention, the crystalline contrast agent essentially consists of a manganese-organic compound comprising repeating coordination entities which can be described with the formula {[Mn$_2$(Cmdcp)$_2$(H$_2$O)$_2$](H$_2$O)} extending in three dimensions (3D framework).

The manganese-organic compound can in particular be described by the formula {[Mn$_2$(Cmdcp)$_2$(H$_2$O)$_2$](H$_2$O)}$_n$ referenced herein as compound 1. Said compound crystallizes in the monoclinic space group P2$_1$/c with each asymmetric unit consisting of one dissociated water and one [Mn$_2$(Cmdcp)$_2$(H$_2$O)$_2$] coordination entity. The two manganese ions contain one fully occupied Mn(1) and two half occupied Mn(2) and Mn(3). Two of the six carboxylate groups of two Cmdcp ligands coordinate to two Mn centers in a monodentate mode, two in bridging bidentate coordination modes to four Mn centers, and the rest two bridging carboxylate groups coordinate to three Mn centers due to two bridging O atoms from two carboxylates of two Cmdcp ligands sharing the same Mn centers. The three Mn atoms in the asymmetric unit adopt an octahedral coordination geometry.

In an alternative embodiment of the present invention, the crystalline contrast agent essentially consists of a gadolinium-organic compound comprising repeating coordination entities which can be described with the formula {[Gd(Cmdcp)(H$_2$O)$_3$](NO$_3$).3H$_2$O} extending in three dimensions (3D framework).

The gadolinium-organic compound can in particular be described by the formula {[Gd(Cmdcp)(H$_2$O)$_3$](NO$_3$).3H$_2$O}$_n$ referenced herein as compound 2. Said compound crystallizes in the monoclinic space group P2$_1$/n and each asymmetric unit consists of one [Gd(Cmdcp)(H$_2$O)$_3$]$^+$ coordination entity cation, one NO$_3^-$ anion and three dissociated water molecules. The Cmdcp ligand is located on the inversion center and coordinates to one Gd center in a chelating mode and to four Gd centers in bridging bidentate coordination modes. Each Gd center is coordinated by one chelating carboxylate and four monodentate carboxylates from five different Cmdcp ligands and three water molecules, thereby forming a monocapped square-antiprism coordination geometry.

The present invention further provides a kit or a pharmaceutically acceptable composition comprising the contrast agent obtained or obtainable with the method described above and at least one pharmaceutically acceptable carrier. The pharmaceutically acceptable carrier can be, for example, a diluent or other excipient including at least one of water like water for injection, saline, dextrose, glycerol, or the like, and combinations thereof. In addition, the kit or pharmaceutically acceptable composition may contain wetting or emulsifying agents, stabilizing or pH-buffering agents, and the like.

The kit or pharmaceutically acceptable composition can contain at least one further active ingredient. The contrast agent may also be coupled to a targeting moiety that can target a region of interest in a subject. The targeting moiety may be selected from proteins, enzymes, peptides, antibodies or the like.

The pharmaceutically acceptable composition can be in either solid or liquid form. It can be a solution or suspension or a solid that is suitable for solution in, or suspension in, a diluent prior to use.

In a further aspect, the present invention provides a method for in vivo imaging of a subject. The expression "imaging of a subject" includes imaging the whole subject or at least one part thereof like a cell, tissue or organ which is generally referred to as the "site to be imaged".

The method for in vivo imaging of the subject comprises:
(i) administering to the subject the crystalline contrast agent obtained or obtainable by the preparation method described above;
(ii) waiting a time sufficient to allow the contrast agent to accumulate at the site to be imaged; and
(iii) imaging the site to be imaged with magnetic resonance imaging for obtaining one or more magnetic resonance images.

The subject can be an animal or a human. Preferably, the subject is a mammal, in particular a human. The site to be imaged preferably includes one or both kidneys.

The crystalline contrast agent can be administered to the subject alone or as part of a pharmaceutically acceptable composition. The relative amounts of the crystalline contrast agent of the invention, a pharmaceutically acceptable carrier, and any additional active ingredients in a pharmaceutically acceptable composition of the invention will vary, depending upon the identity, size, and condition of the subject and upon the administration route. The contrast agent may also be coupled to a targeting moiety that can target a region of interest in the subject such as proteins, enzymes, peptides, antibodies and the like.

Suitable pharmaceutically acceptable compositions can be, for example, solutions or suspensions, or they may be in the form of a solid that is suitable for solution in, or suspension in, a diluent prior to administration. They may be adapted for administration by any convenient peripheral route, such as parenteral or oral administration. The crystalline contrast agent of the invention, optionally comprising other pharmaceutically active compounds, is preferably administered to the subject parenterally, in particular orally or intravenously.

The amount of agent administered depends on the crystalline contrast agent, the subject and its condition and, for example, the site to be imaged and can be determined in accordance with normal clinical practice. Typically, the dosage of the contrast agent is in the range up to about 500 μM, as this ensures good biocompatibility and low cytotoxicity while producing exceptional imaging properties. Dosages may be given in single dose regimes, split dose regimes and/or in multiple dose regimes lasting over several days.

The crystalline contrast agent obtained or obtainable by the preparation method preferably essentially consists of a manganese-organic compound comprising repeating coordination entities which can be described with the formula $\{[Mn_2(Cmdcp)_2(H_2O)_2](H_2O)\}$ extending in three dimensions. The manganese-organic compound is in particular a manganese-organic compound which can be described by the formula $\{[Mn_2(Cmdcp)_2(H_2O)_2](H_2O)\}_n$ referenced herein as compound 1.

In embodiments of the present invention, step (iii) of the method for in vivo imaging of the subject comprises utilizing a contrast-enhancing imaging pulse sequence which may comprise a fast spin echo sequence or a spoiled gradient echo sequence. Preferably, said contrast-enhancing imaging pulse sequence comprises a spoiled gradient echo sequence. Such technique is known in the art, wherein manufacturers of magnetic resonance imaging equipment use different names for this technique like FLASH (fast low angle shot magnetic resonance imaging technique), SPGR (Spoiled Gradient Echo), CE-FFE-T1 (Contrast-Enhanced Fast Field Echo) or T1-FFE.

In another aspect, the present invention refers to the use of the crystalline contrast agent, in particular essentially consisting of compound 1 or compound 2, or a kit or pharmaceutically acceptable composition comprising the crystalline contrast agent, in particular essentially consisting of compound 1 or compound 2, for in vivo imaging of a subject by means of magnetic resonance imaging.

EXAMPLES $H_3CmdcpBr$ was synthesized according to Chen, J. X. et al. (Bent tritopic carboxylates for coordination networks: clues to the origin of self-penetration, Cryst Eng Comm. 16(2014) 7722-7730). All the other reagents and solvents were obtained from commercial sources and used without further purification.

IR spectra were recorded on a Nicolet MagNa-IR 550 infrared spectrometer. Elemental analyses for C, H, and N were performed on an EA1110 CHNS elemental analyzer. Thermogravimetric analysis (TGA) was performed on an SDTA851 Thermogravimetric Analyzer at a heating rate of 10° C. $min^{-1}$ under a nitrogen gas flow in an $Al_2O_3$ pan. Powder X-ray diffraction (PXRD) spectra were recorded with a Rigaku D/max-2200/PC. The X-ray generated from a sealed Cu tube was mono-chromated by a graphite crystal and collimated by a 0.5 mm MONOCAP (λ Cu-Kα=1.54178 Å). The tube voltage and current were 40 kV and 40 mA, respectively. MRI measurements were performed on a 0.5 T MRI system (SPEC-RC2, Beijing SPEC Corp.).

Human embryonic kidney cell line (HEK 293) was purchased from the cell bank of Chinese Academy of Sciences (Shanghai, China), which was routinely cultured in ATCC-formulated DMEM (Invitrogen) modified containing 10% fetal bovine serum (FBS) and 1% antibiotics (penicillin streptomycin, 10,000 U $mL^{-1}$) in 150 mm diameter Primaria dishes at 37° C. with saturated humidity and 5% $CO_2$. The medium was changed every 24~48 h. Healthy, young, non-pregnant and nulliparous Kunming mice (20~22 g) for in vivo toxicity analysis were purchased from the Laboratory Animal Center, Southern Medical University, China.

The animal experiment's protocols approved by Administrative Panel on Laboratory Animal Care (APLAC) at Stanford University were performed in accordance with the recommendations of the American Association for the Accreditation of Laboratory Animal Care. Female nude mice (6~8 weeks, 18±2 g, Charles River Laboratories) were used for in vivo studies.

Example 1A

Preparation of Crystalline Contrast Agents of the Present Invention

Preparation of $\{[Mn_2(Cmdcp)_2(H_2O)_2](H_2O)\}_n$ (Compound 1)

$H_3CmdcpBr$ (92 mg, 0.3 mmol) was suspended in $H_2O$ (25 mL) and the pH was adjusted to 7.0 with 0.1 M NaOH. Then a solution of $MnCl_2$ (38 mg, 0.3 mmol) in $H_2O$ (20 mL) was added. The resulting mixture was stirred at 100° C. for 0.5 h, cooled to ambient temperature and then filtered. The obtained clear light yellow solution was allowed to stand at room temperature for several days. The formed yellow crystals were collected by filtration and dried in vacuum to give compound 1 (78 mg, 85%). Anal. Calcd. for $C_{18}H_{16}Mn_2N_2O_{15}$: C, 35.43; H, 2.64; N, 4.59. found: C, 35.13; H, 2.74; N, 4.48. IR bands (KBr disc, $cm^{-1}$) v 3394 (s), 3203 (s), 3014 (s), 2947 (s), 1669 (s), 1622 (s), 1601 (s), 1446 (m), 1384 (s), 1356 (s), 1232 (w), 1174 (w), 1135 (w), 1027 (w), 912 (w), 782 (m), 768 (m), 739 (m), 727 (m), 718 (m), 628 (m), 577 (w).

Preparation of $\{[Gd(Cmdcp)(H_2O)_3](NO_3)\cdot 3H_2O\}_n$ (Compound 2)

A solution of $H_3CmdcpBr$ (28 mg, 0.09 mmol) in $H_2O$ (5 mL) was adjusted to pH 6.0 with 0.1 M NaOH solution. Then, a solution of $Gd(NO_3)_3\cdot 6H_2O$ (27 mg, 0.06 mmol) in $H_2O$ (1 mL) was added. The clear, colorless solution was stirred for 0.5 h and then allowed to stand at room temperature for one week. The formed colorless crystals were collected by filtration and dried in vacuum to afford compound 2 (31 mg, 56%). Anal. Calcd. for $C_9H_{17}GdN_2O_{15}$·$2H_2O$: C, 21.01; H, 2.55; N, 5.45. found: C, 20.69; H, 2.01; N, 5.81. IR bands (KBr disc, $cm^{-1}$) v 3410 (s), 1647 (s), 1610 (s), 1390 (s), 1238 (m), 1175 (w), 1114 (w), 935 (m), 770 (m), 728 (m), 630 (m), 520 (m).

Example 1B

Characterization of the Prepared Crystalline Contrast Agents

Figure 1B:
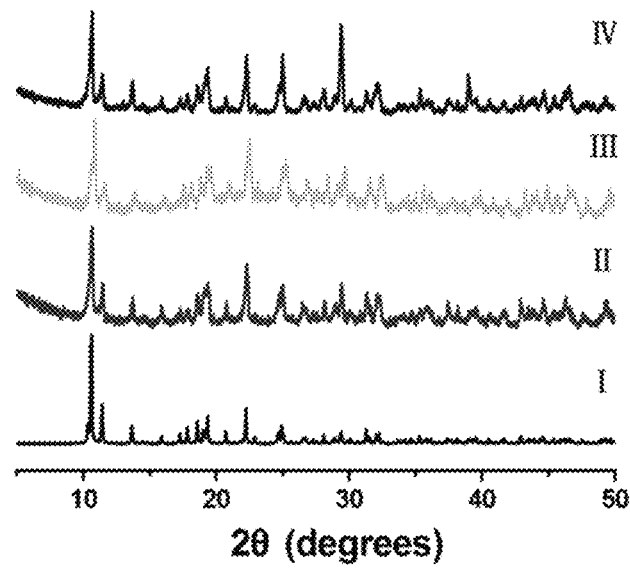
FIG. 1B shows powder X-ray diffraction patterns of $\{[Gd(Cmdcp)(H_2O)_3](NO_3).3H_2O\}_n$ (compound 2) showing agreement between the simulated (I), synthesized (II), the fresh powder immersed in $H_2O$ for 24 h (III) and the fresh powder immersed in rats' serum for 24 h (IV).
Figure 8A:
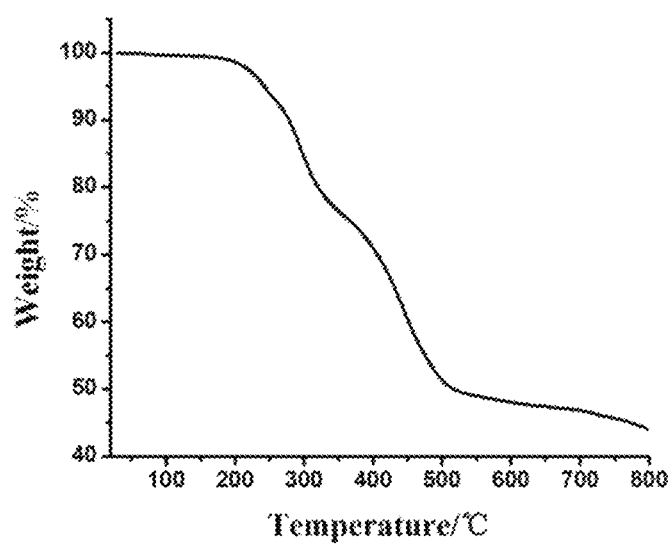
FIG. 8A refers to the results of the thermogravimetric analysis of compounds 1 and 2 by providing a curve illustrating the results of the thermogravimetric analysis of compound 1.
Figure 8B:
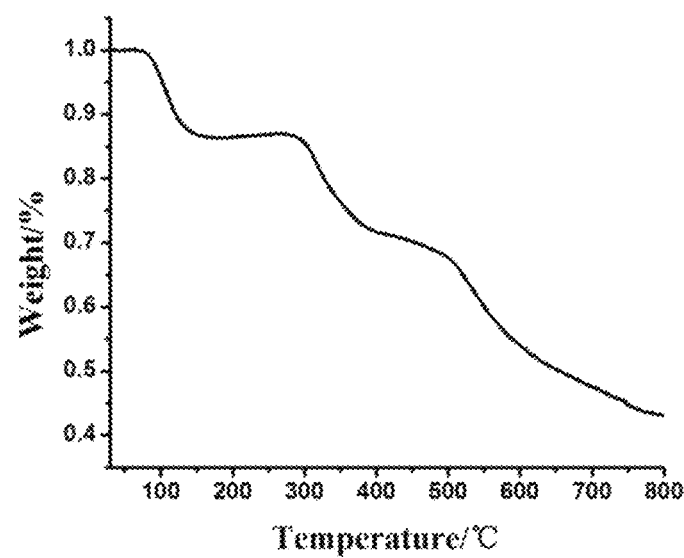
FIG. 8B is a curve illustrating the results of the thermogravimetric analysis of compound 2.
Figure 9A:
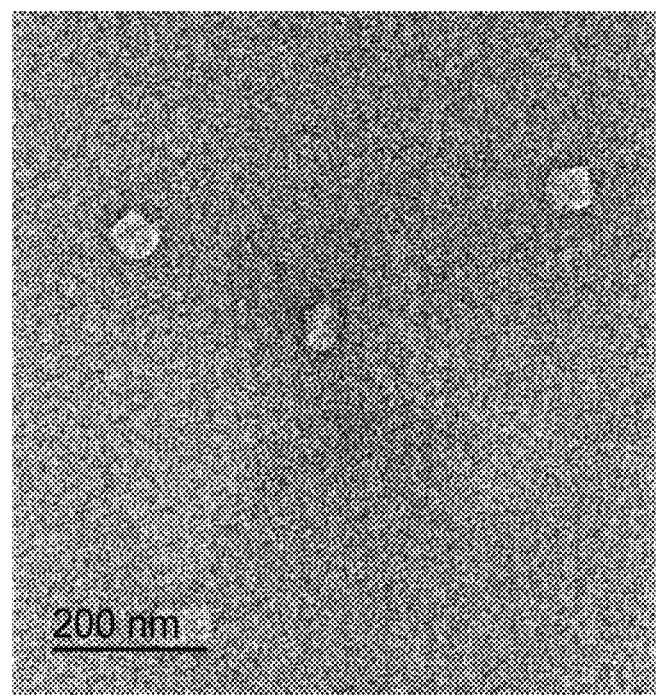
FIG. 9A shows transmission electron microscopy (TEM) image of compounds 1
Figure 9B:
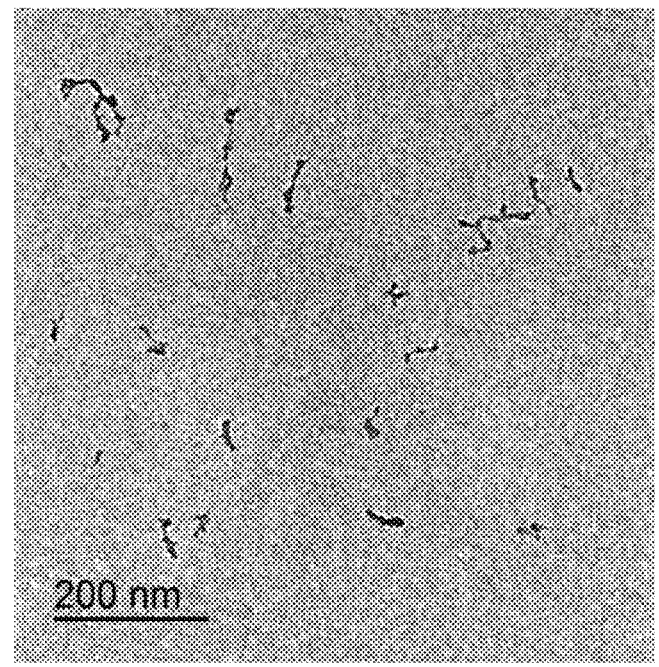
FIG. 9B is a TEM image of compound 2.

Compounds 1 and 2 obtained from the reaction of $H_3CmdcpBr$ with $MnCl_2$ and $Gd(NO_3)_3 \cdot 6H_2O$ in the presence of NaOH are air and moisture stable under aerobic conditions. Upon ultrasonication, compounds 1 and 2 show good water-solubility with the maximum concentrations up to 2 mM for compound 1 and 500 µM for compound 2, respectively. The powder X-ray diffraction (PXRD) pattern of a fresh powder of compound 1 or compound 2 immersed in $H_2O$ or rats' serum for 24 h, are in agreement with that of the simulated one, indicating their bulky phase purity and stability (PXRD, FIGS. 1A and 1B). Their bulk phase purity was further confirmed by FT-IR and elemental analyses. Thermogravimetric analysis (TGA) indicated that both compound 1 and compound 2 are stable up to 250° C. and 300° C. For compound 1, the weight loss of 8.96% from 30° C. to 272° C. corresponds to the loss of one lattice water molecule and two coordinated water molecules (calculated 8.85%). For compound 2, the weight loss of 13.17% from 30° C. to 150° C. corresponds to the loss of one lattice water molecule and three coordinated water molecules (calculated 13.21%) and the other two lattice water molecules may be lost during the drying process (FIGS. 8A and 8B). TEM micrographs for fresh compound 1 obtained from water gave the size of ca 50 nm in diameter and compound 2 is mainly composed of particles that appear silk-like shapes with 70 nm in length and 4 nm in diameter (FIGS. 9A and 9B).

Example 1C

X-Ray Crystal Structure Determinations of the Prepared Crystalline Contrast Agents Crystallographic measurements were made on a Bruker APEX II diffractometer by using graphite-monochromated Mo Kα (λ=0.71073 Å) irradiation for compound 1 and compound 2. The data were corrected for Lorentz and polarization effects with the SMART suite of programs and for absorption effects with SADABS (Sheldrick, G. M., SADABS, program for empirical absorption correction of area detector data, University of Göttingen: Göttingen, Germany, 1996). All the crystal structures were solved by direct methods and refined on $F^2$ by full-matrix least-squares techniques with SHELXTL-97 program (Sheldrick, G. M., SHELXS-97 and SHELXL-97, programs for crystal structure solution and refinement, University of Göttingen: Göttingen, Germany, 1997). For compound 1, the location of the hydrogen atoms on the coordinated and free water were suggested by Calc-OH program in WinGX suite, and the water molecules were subsequently refined as rigid groups with O–H=0.85 Å and thermal parameters constrained to $U_{iso}(H)=1.2U_{eq}(O)$. For compound 2, the hydrogen atoms on the waters were found from Fourier Map and applied O–H=0.82 Å and $U_{iso}(H)=1.5U_{eq}$ (O) for the bond length and the thermal parameters, respectively. All the non-hydrogen atoms were refined anisotropically. CCDC numbers for compound 1 and compound 2 are U.S. Pat. Nos. 1,057,253 and 1,057,254. A summary of the key crystallographic information for compound 1 and compound 2 is given in Table 1.

TABLE 1

Crystallographic data for compounds 1 and 2

| | Compound | |
|---|---|---|
| | 1 | 2 |
| Molecular formula | $C_{18}H_{16}Mn_2N_2O_{15}$ | $C_9H_{17}GdN_2O_{15}$ |
| Formula weight | 610.21 | 550.5 |
| Crystal system | monoclinic | monoclinic |
| Space group | P2(1)/c | P2(1)/n |
| a (Å) | 7.5910(5) | 10.1468(6) |
| b (Å) | 17.6666(12) | 15.5239(9) |
| c (Å) | 15.5193(11) | 10.5159(6) |
| α (°) | 90 | 90 |
| β (°) | 98.904(2) | 102.2020(10) |
| γ (°) | 90 | 90 |
| V (Å$^3$) | 2056.2(2) | 1619.02(16) |
| Z | 4 | 4 |
| T/K | 296(2) | 296(2) |
| $D_{calc}$ (g cm$^{-3}$) | 1.971 | 2.258 |
| λ (Mo-Kα) (Å) | 0.71075 | 0.71073 |
| µ (cm$^{-1}$) | 1.32 | 4.185 |
| Total reflections | 20974 | 10257 |
| Unique reflections | 4700 | 2918 |
| No. Observations | 3723 | 2687 |
| No. Parameters | 337 | 280 |
| R$^a$ | 0.0527 | 0.0236 |
| wR$^b$ | 0.1004 | 0.0651 |
| GOF$^c$ | 1.112 | 1.108 |
| Δρ$_{max}$ (e Å$^{-3}$) | 0.835 | 1.812 |
| Δρ$_{min}$ (e Å$^{-3}$) | −0.565 | −1.374 |

$^a$R = Σ||F$_o$| − |F$_c$|/Σ|F$_o$||.
$^b$wR = {Σw(F$_o^2$ − F$_c^2$)$^2$/Σw(F$_o^2$)$^2$}$^{1/2}$.
$^c$GOF = {Σ[w((F$_o^2$ − F$_c^2$)$^2$)/(n − p) }$^{1/2}$, where n = number of reflections and p = total numbers of parameters refined.
Crystal structure of {[Mn$_2$(Cmdcp)$_2$(H$_2$O)$_2$](H$_2$O)}$_n$ (compound 1)

Figure 2A:
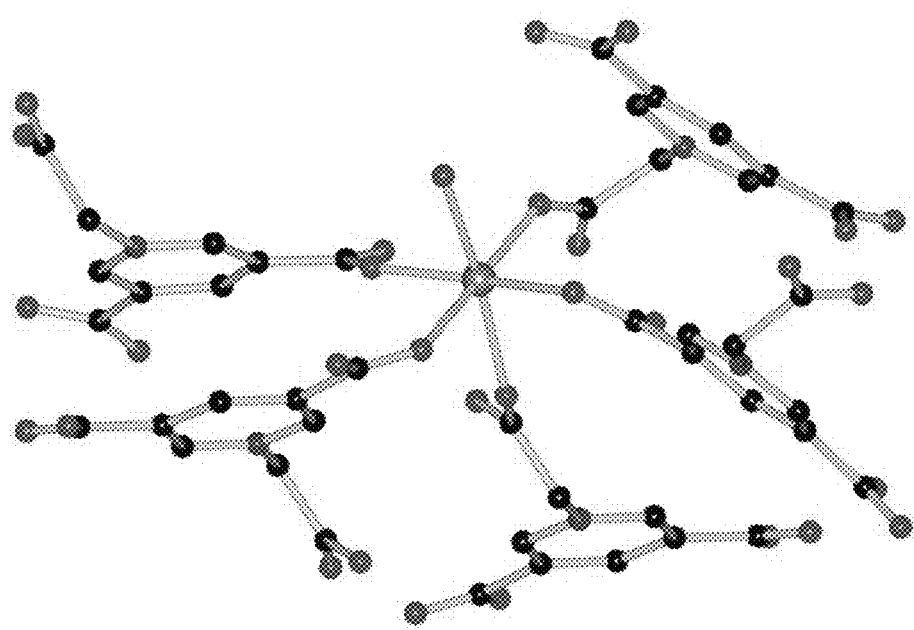
FIG. 2A illustrates the three dimensional structure of compound 1 by illustrating the coordination environment of Mn(1).
Figure 2B:
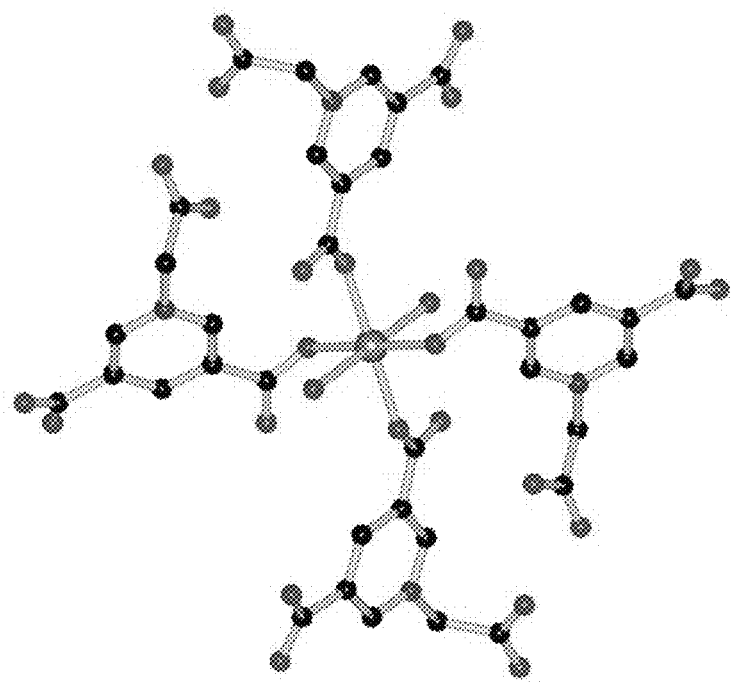
FIG. 2B illustrates the coordination environment of Mn(2).
Figure 2C:
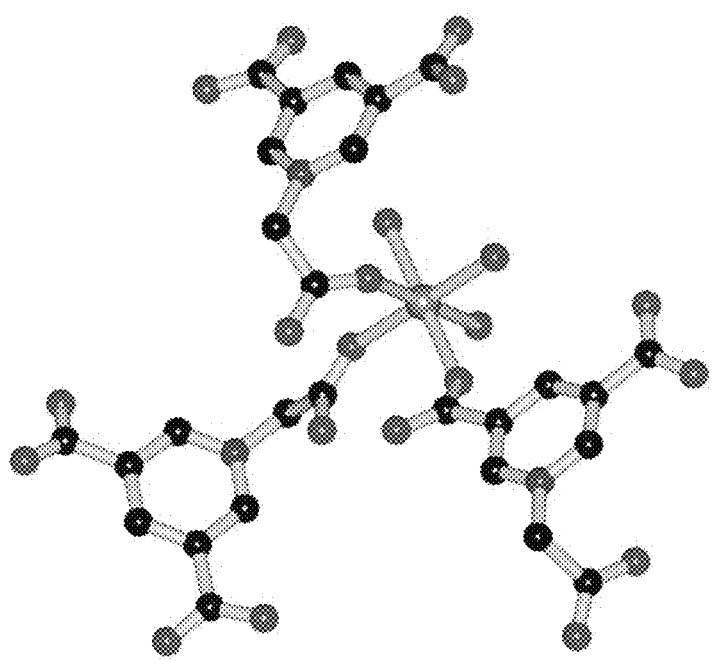
FIG. 2C illustrates the coordination environment of Mn(3).
Figure 2D:
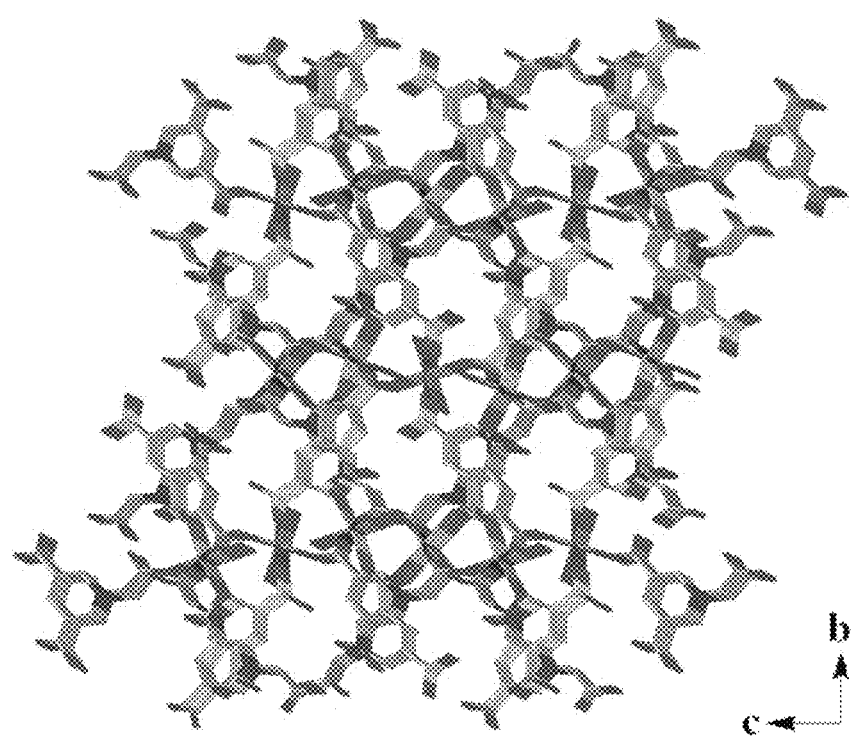
FIG. 2D shows the three dimensional structure of compound 1 as viewed along the a axis and the dissociated water molecules are omitted.
Figure 2E:
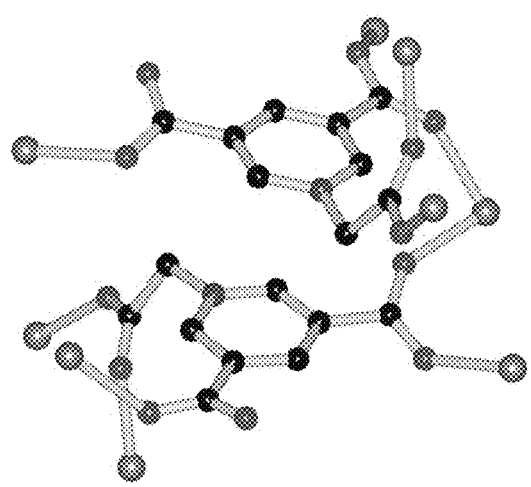
FIG. 2E shows the linking mode of two Cmdcp ligands in the asymmetric unit to nine different Mn centers. Color codes: Mn teal, O red, N blue, C black in FIG. 2A to 2C, gray in FIG. 2D.

Compound 1 crystallizes in the monoclinic space group P2$_1$/c and each asymmetric unit consists of one dissociated water and one [Mn$_2$(Cmdcp)$_2$(H$_2$O)$_2$] molecule. The two Mn ions contain one fully occupied Mn(1) and two half occupied Mn(2) and Mn(3). Two of the six carboxylate groups of two Cmdcp ligands coordinate to two Mn centers in a monodentate fashion, two in bridging bidentate coordination modes to four Mn centers, and the rest two bridging carboxylate group coordinate to three Mn centers due to that two bridging O atoms from two carboxylates of two Cmdcp ligands sharing the same Mn centers. The two Cmdcp ligands thus act as a nine-connected node (FIG. 2E).

It is notable that the three Mn atoms in the asymmetric unit adopt the same octahedral coordination geometry, but with different coordination environments. The octahedron were completed with five monodentate carboxylates and one water for Mn(1) (FIG. 2A), four monodentate carboxylates and two waters for Mn(2) (FIG. 2B), three monodentate carboxylates and three waters for Mn(3) (FIG. 2C). Therefore, the Mn(1) center acts as a five-connected node in a topological perspective, the Mn(2) center acts as a four-connected node whereas the Mn(3) center a three-connected node, accompanying with two ligands nine-connected node, leading to a 3D framework (FIG. 2D).

Crystal Structure of {[Gd(Cmdcp)(H$_2$O)$_3$](NO$_3$) .3H$_2$O}$_n$ (Compound 2)

Figure 3A:
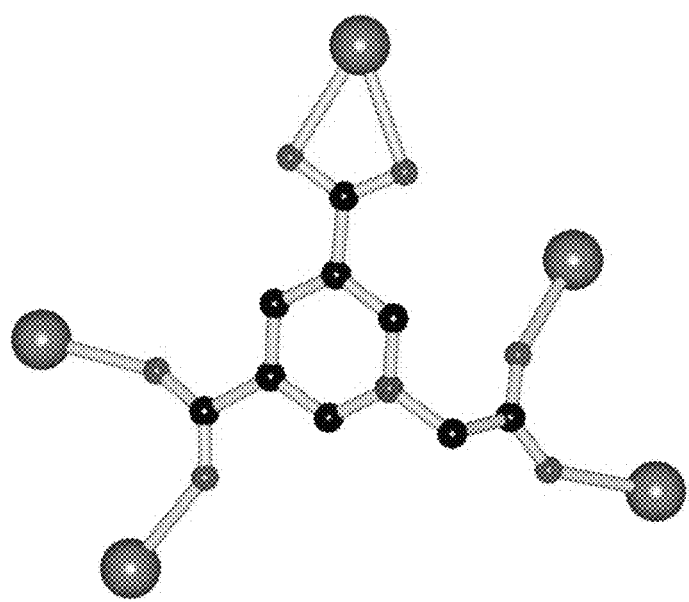
FIG. 3A illustrates the three dimensional structure of compound 2 by illustrating the linking of the Cmdcp ligand to five different gadolinium centers.
Figure 3B:
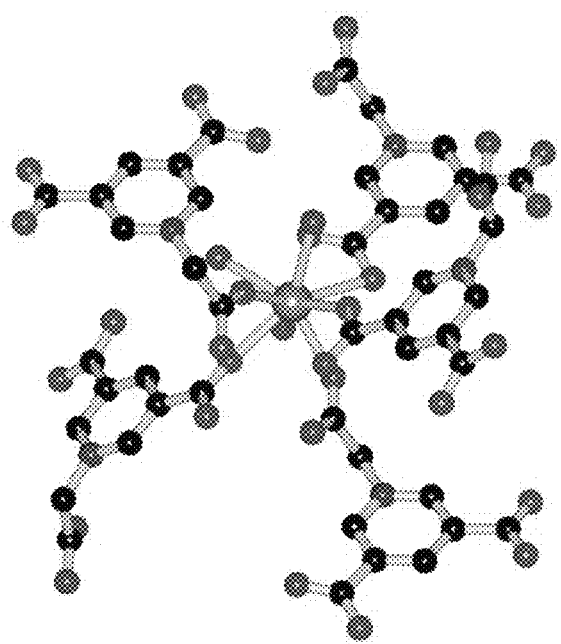
FIG. 3B shows the coordination environment of the $Gd^{3+}$ ion.
Figure 3C:
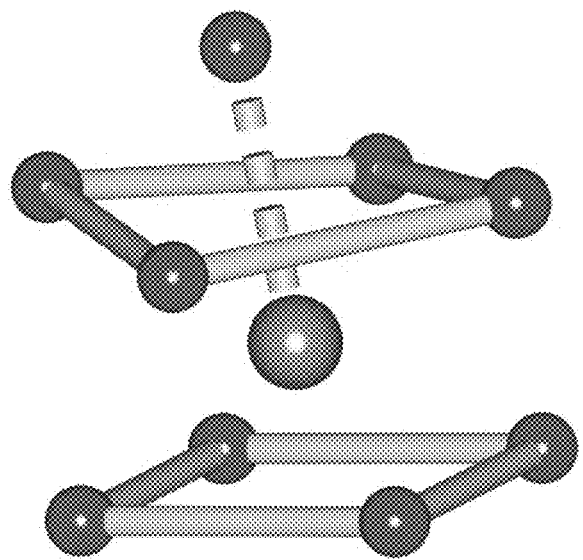
FIG. 3C illustrates the monocapped square-antiprismatic coordination geometry of the $Gd^{3+}$ ion.
Figure 3D:
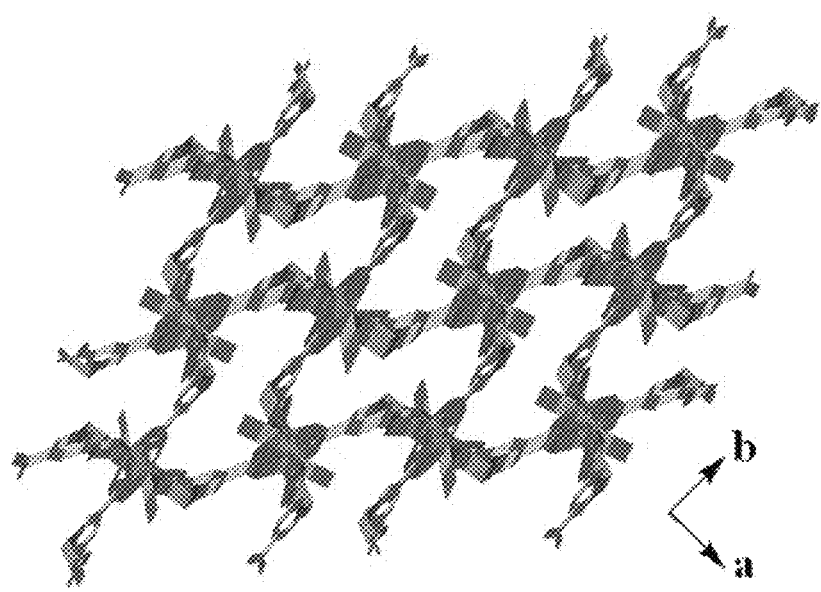
FIG. 3D illustrates the 3D structure of compound 2 as viewed along the c axis and the $NO_3^-$ and dissociated water molecules are omitted. Color codes: Gd teal, O red, N blue, C black in FIG. 3A to 3B, gray in FIG. 3D.

Compound 2 crystallizes in the monoclinic space group P2$_1$/n and each asymmetric unit consists of one [Gd(Cmdcp)(H$_2$O)$_3$]$^+$ cation, one NO$_3^-$ anion and three dissociated water molecules. As shown in FIG. 3A, the Cmdcp ligand is located on the inversion center and coordinates to one Gd center in a chelating fashion and to four Gd centers in bridging bidentate coordination fashion. Each Gd center is coordinated by one chelating carboxylate and four monodentate carboxylates from five different Cmdcp ligands and three water molecules, thereby forming a monocapped square-antiprism coordination geometry as shown in FIGS. 3B and 3C. The Cmdcp ligand thus acts as a five-connected node, whereas the Gd center also acts as a five-connected node, leading to a 3D framework (FIG. 3D).

Example 2

Longitudinal Relaxation Time Measurement

The measurement of the longitudinal relaxation time $T_1$ was conducted at 30° C. Five samples of compounds 1 and 2 were prepared with the concentrations of 31.25, 62.5, 125, 250, and 500 μM in deionized water, respectively. Before the $T_1$ test, these samples were ultrasonicated for 2 min to dissolve the compounds homogeneously in deionized water. The $T_1$ of deionized water was tested as background. The $T_1$ of the MOF solution was corrected from the background. The measurement time of each sample was ca. 2 min. Relaxivity, $r_1$ ($mM^{-1} \cdot s^{-1}$), is defined as the slope of the plot of $1/T_1$ versus the concentration of compounds 1 and 2. $T_1$ mapping images were acquired using an inversion recovery sequence (TE/TR=11/4000 ms) with inversion time ($T_I$) of 200, 300, 400, 500, 600, and 700 ms. On each image, signal intensities were measured by drawing ROIs in the center of each vial. The $T_1$ relaxation times were performed by fitting the acquired inversion recovery images to a following equation: $M=M_0 (1-2\exp(-T_I/T_1)+\exp(-TR/T_1))$, where M and $M_0$ are measured and initial magnetization, respectively. All data fittings were performed using a nonlinear least-squares algorithm implemented in the Origin Pro 8.1 SR2 (OriginLab Co.) analysis software.

Figure 4A:
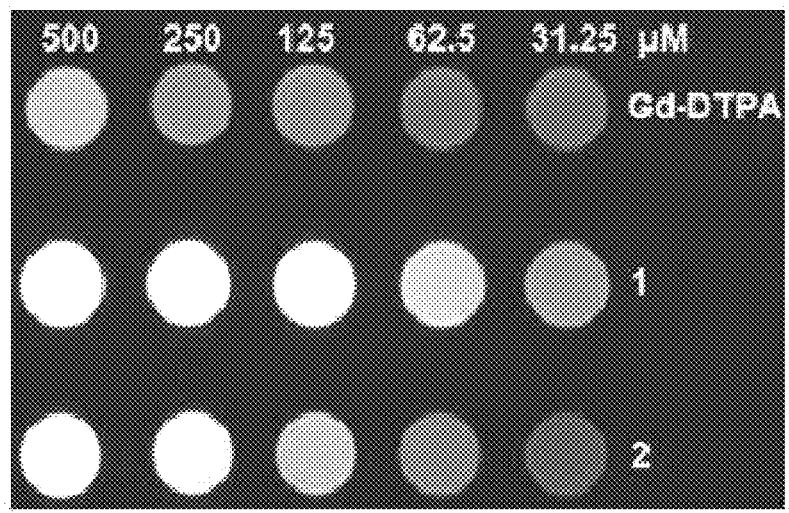
FIG. 4A shows $T_1$-weighted MRI images of compounds 1 and 2 and Gd-DTPA of varying concentrations in water (compound 1 referenced as "1" and compound 2 referenced as "2").
Figure 4B:
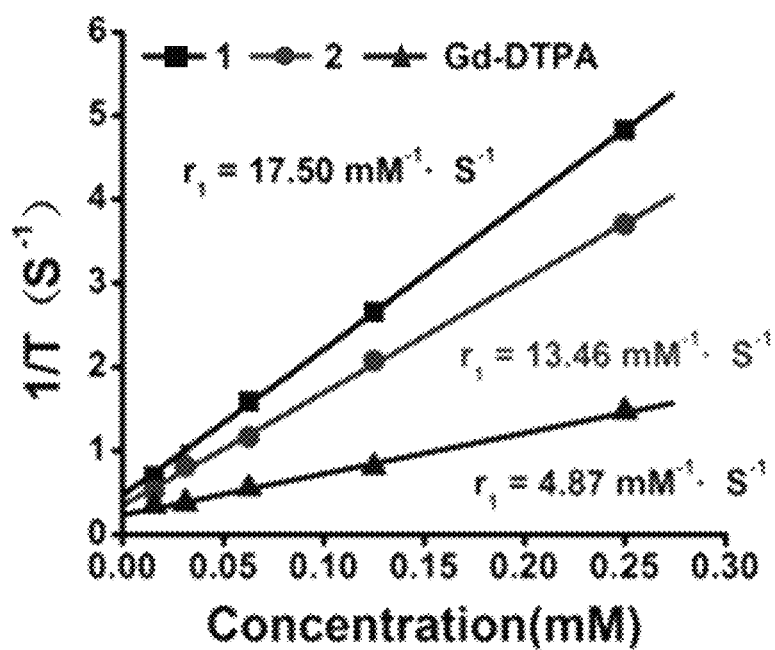
FIG. 4B shows the $r_1$ relaxivity curves of compounds 1 (curve "1") and 2 (curve "2") and Gd-DTPA.
Figure 10A:
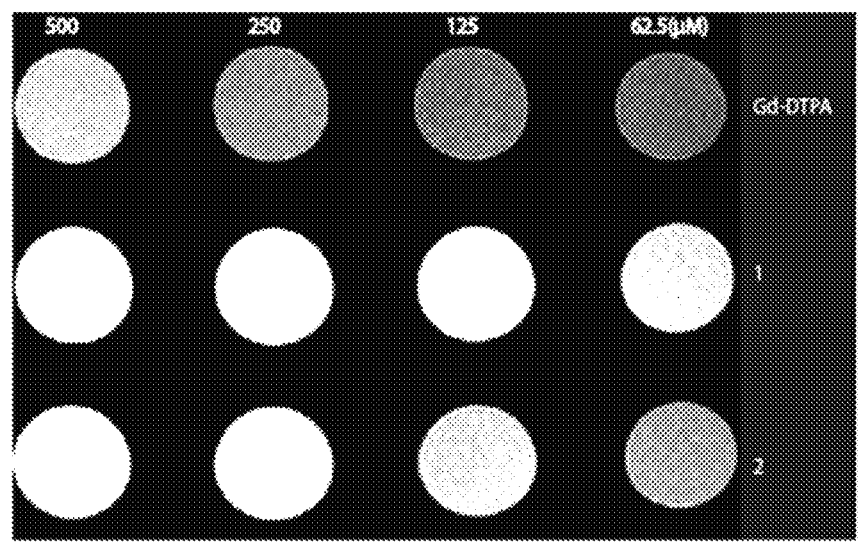
FIGS. 10A and 10B refer to the MRI phantom measurement at 3T, with FIG. 10A showing $T_1$ weighted MR Images of compounds 1 and 2 (compound 1 referenced as "1" and compound 2 referenced as "2") and Gd-DTPA of varying concentrations in water.
Figure 10B:
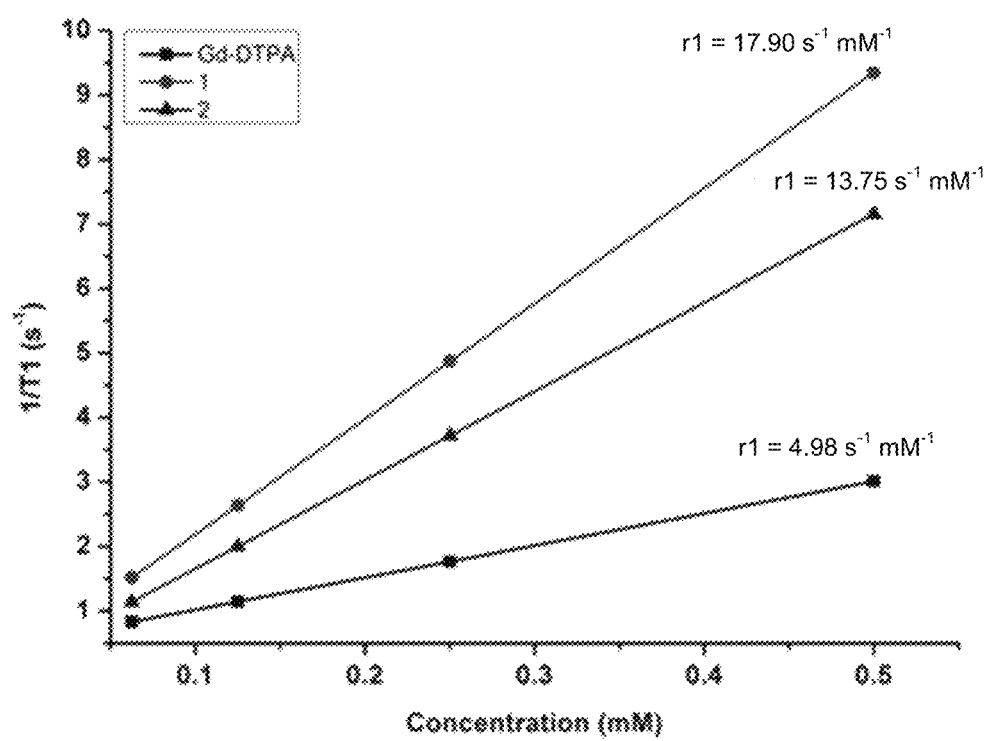

The $T_1$-weighted images and relaxivity of compounds 1 and 2 have been measured and FIG. 4A shows the $T_1$-weighted images of compounds 1 and 2, and Gd-DTPA as a positive control, in the concentration range from 31.25 to 500 μM. It is clear that the MRI signal intensity increased with the increase in their concentrations. The linear relationship between $1/T_1$ and the concentrations gave the relaxivity data with the $r_1$ values being 17.50 $mM^{-1} \cdot s^{-1}$ for compound 1, 13.46 $mM^{-1} \cdot s^{-1}$ for compound 2 and 4.87 $mM^{-1} \cdot s^{-1}$ for Gd-DTPA, respectively (FIG. 4B). Their relaxivities at 3T are slightly higher than those at 0.5T (FIGS. 10A and 10B), indicating that the high field strength does not significantly affect their contrast enhancement. Evidently, compounds 1 and 2 exhibit much higher signal enhancement ability than Gd-DTPA. It should also be noted that both compound 1 and 2 exhibit much higher $r_1$ relaxivities than clinically used small-molecule contrast agent OmniScan (4.1 $mM^{-1} \cdot s^{-1}$) (Rieter, W. J. et al., Nanoscale metal-organic frameworks as potential multimodal contrast enhancing agents, J. Am. Chem. Soc. 128(2006) 9024-9025) and reported nanoscale gadolinium MOFs [$Gd_2$(bhc)($H_2O$)$_6$] (bhc=benzenehexacarboxylate, 1.5 $mM^{-1} \cdot s^{-1}$) (Taylor, K. M. et al., Surfactant-assisted synthesis of nanoscale gadolinium metal-organic frameworks for potential multi-modal imaging, Angew Chem. Int. Ed. Engl. 47(2008) 7722-7725). This value is comparable to $Gd(BDC)_{1.5}(H_2O)_2$ (BDC=1,4-benzenedicarboxylate, 20.1 $mM^{-1} \cdot s^{-1}$) with ~1 μm in length and ~100 nm in diameter. These results suggest that compounds 1 and 2 are exploitable as promising MRI agents due to the presence of large payloads of paramagnetic $Mn^{2+}$ and $Gd^{3+}$. In addition, the good water solubility ensures accessibility of the gadolinium or manganese centers to bulk water and contributes to the $r_1$ relaxivities and $T_1$-weighted images.

Example 3

MTT Assay

The cytotoxicity of compounds 1 and 2 was evaluated against normal human embryonic kidney cell line HEK 293 by using MTT assay. The cells were cultured in DMEM medium with 10% fetal bovine serum (FBS), 100 μg/mL streptomycin and 100 U/mL penicillin at 37° C. with 5% $CO_2$. After centrifugation at 1500×g for 5 min, cell pellets were re-suspended in respective medium at the concentration of $3 \times 10^4$ cells/mL and seeded in 96-well plates at 100 μL with $3 \times 10^4$ cells/well. Compounds 1 and 2 and Gd-DTPA (positive control) were diluted with distill water and applied in the final concentrations from 15.625 μM to 500 μM (four wells for each concentration per plate). Plates were incubated for 72 h, and then MTT was added to a final concentration of 0.5 mg/mL per well followed by additional incubation for 4 h. Then the reaction was stopped and the formazan dye was solubilized by adding 150 μL of DMSO. The optical density was measured at 490 nm using a Bio-Rad 3500 microplate reader (Bio-Rad, Hercules, Calif., USA). Each experiment was carried out three times, and the mean values were taken. The data were reported as mean±SD and all the statistical analyses were performed by SPSS11.0. The significant difference between the experimental and control groups was evaluated by T-test method and identified by P<0.05. The cell viability was calculated as follows:

Cell viability (%)=[($OD_1-OD_3$)/($OD_2-OD_3$)]×100

Wherein $OD_1$, $OD_2$ and $OD_3$ are the optical densities of cell culture with sample, without sample and of the medium, respectively.

Figure 5A:
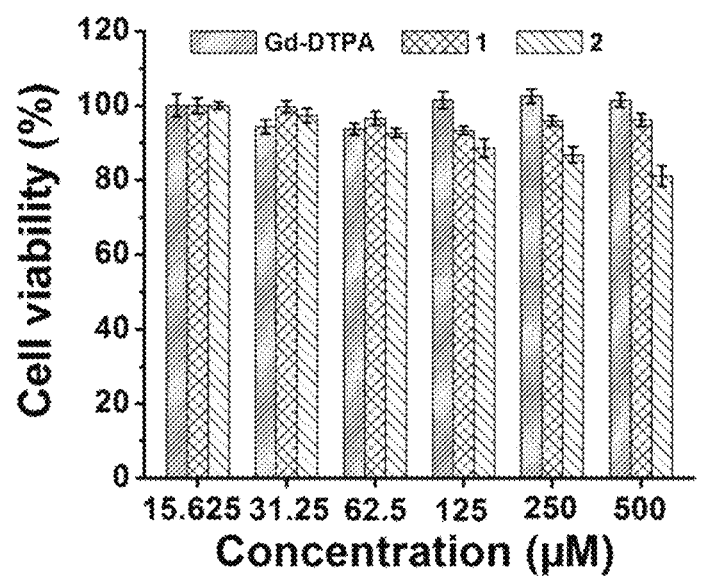
FIG. 5A refers to the cytotoxicity of compounds 1 and 2 by providing a diagram showing the viability of HEK293 cells incubated for 48 h with Gd-DTPA, compounds 1 ("1") and 2 ("2") of varying concentrations.
Figure 5B:
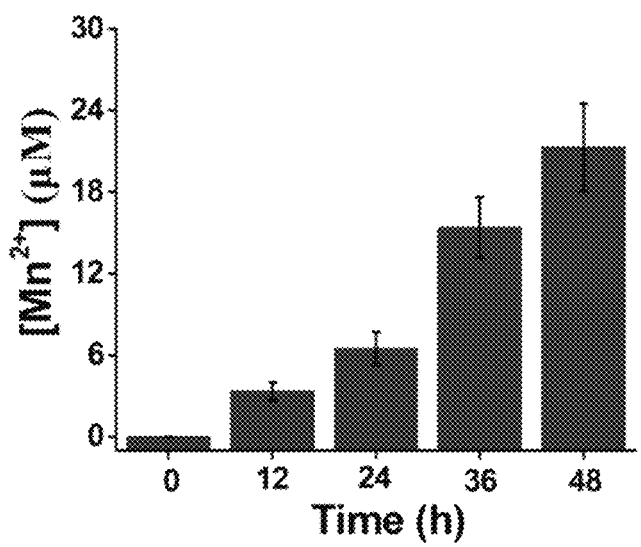
FIG. 5B is a diagram referring to the concentration of free $Mn^{2+}$ obtained at different time with concentrations of 500 μM for compound 1.
Figure 5C:
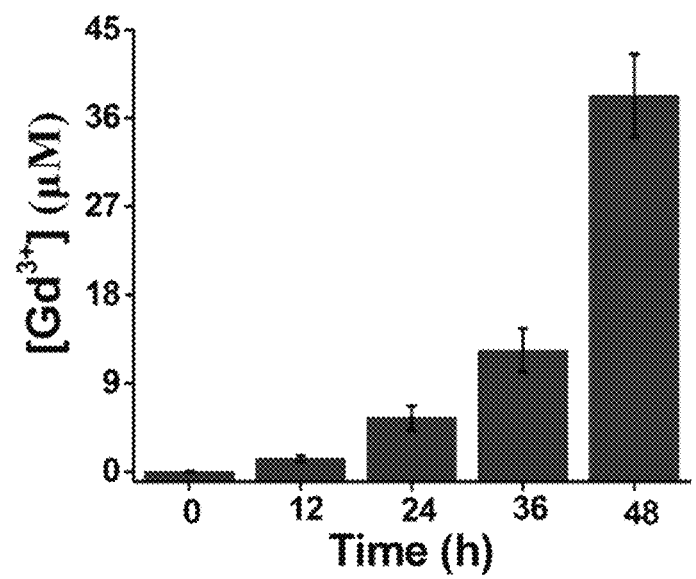
FIG. 5C is a diagram referring to the concentration of free $Gd^{3+}$ obtained at different time with concentrations of 500 μM for compound 2.

The viability of HEK293 cells incubated with compounds 1 and 2 of varying concentrations evaluated using MTT assay (FIG. 5A) proved that there was no significant decrease in the viability of the HEK293 cells at the concentration below 500 μM. At the concentration of 500 μM, the cell viability was estimated to be 95±5% for compound 1 and 80±3% for compound 2. Therefore, compounds 1 and 2 showed good biocompatibility and little cytotoxicity against the model cell line when the drug concentration was below 500 μM. After dissolving compounds 1 and 2 in water with concentrations of 500 μM in 48 h, ICP-MS results (FIG. 5B to 5C) showed that the leakage rate is 4.2% for $Mn^{2+}$ (21 μM) and 7.6% for $Gd^{3+}$ (38 μM), respectively. Such low leakage rate may be a consequence of their low cytotoxicity.

Example 4

In Vivo MRI

Female nude mice (6~8 weeks, 18±2 g, n=3, Charles River Laboratories) performed in vivo MRI was injected via the tail vein with compound 1 (300 uL, 2.7 mg Mn/kg mouse body weight), using a 7.0 T small animal MRI scanner with magnetic bore size of 310 mm, including a superconducting magnet (Magnex Scientific) with 7.0 T field strength and a gradient with 600 mT/m of maximum gradient amplitude, and 6000 T/m/s of a maximum slew rate. T1-weighted MR images of liver and kidney were acquired using fast-spin echo sequence with the following parameters: echo time (TE)/repetition time (TR): 10/750 ms, 256×256 matrix, NEX=1, Field of View (FOV): 4 cm, and slice thickness: 1.0 mm. Three dimensional (3D) contrast enhanced MR angiography of aorta, renal artery and inferior vena cava was performed by using the 3D fast spoiled gradient echo (3D-FSPGR) with the following parameters: echo time (TE)/repetition time (TR): 1.7/5.3 ms, 256×256 matrix, 3 NEX, field of view (FOV): 4 cm and slice thickness: 0.5 mm.

Figure 6A:
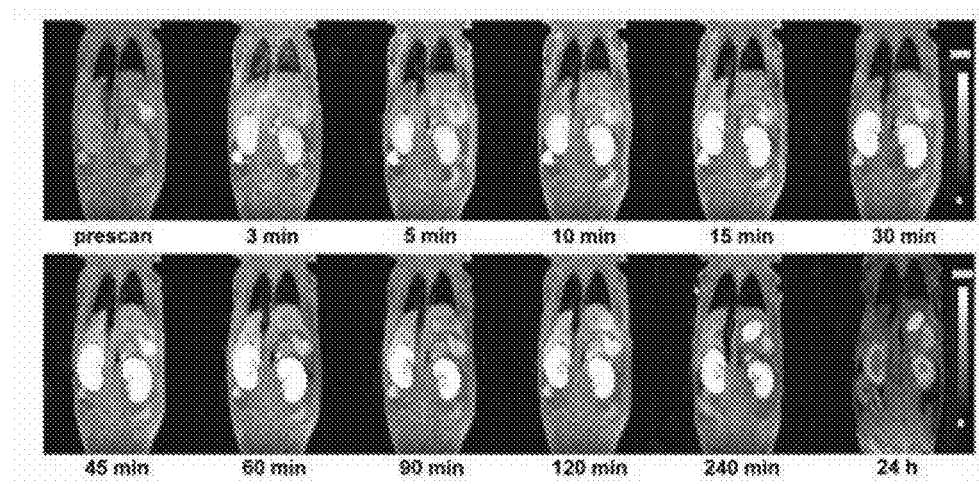
FIG. 6A refers to magnetic resonance (MR) measurements with compound 1 by showing the MR signal intensity from a dynamic study of normal kidneys after intravenous administration of compound 1.
Figure 6B:
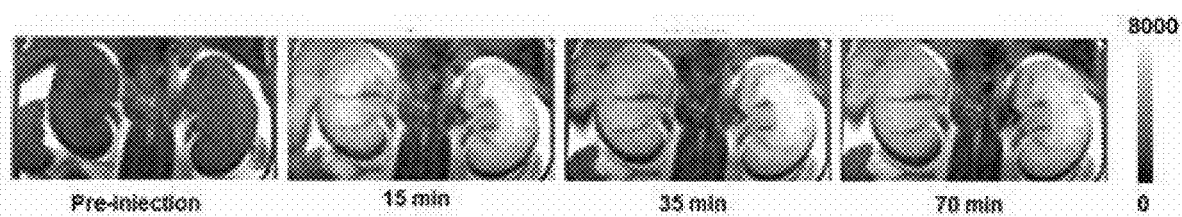
FIG. 6B shows representative $T_1$ weighted images with fast spin echo sequence from a dynamic compound 1 contrast-enhanced MR study of both normal kidneys.
Figure 6C:
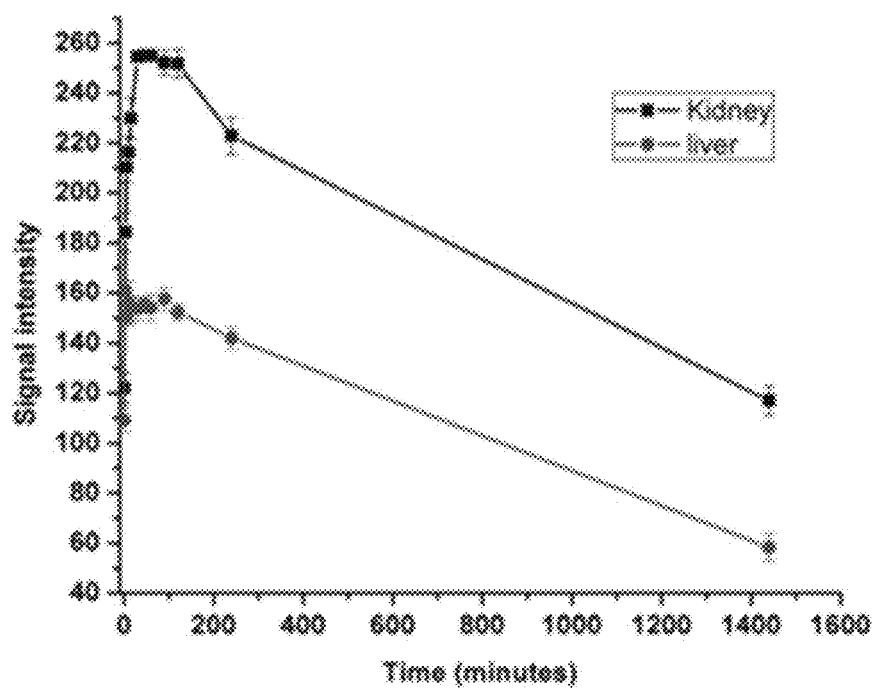
FIG. 6C shows the MR signal intensity from a dynamic study of normal kidneys and liver after intravenous administration of compound 1.
Figure 6D:
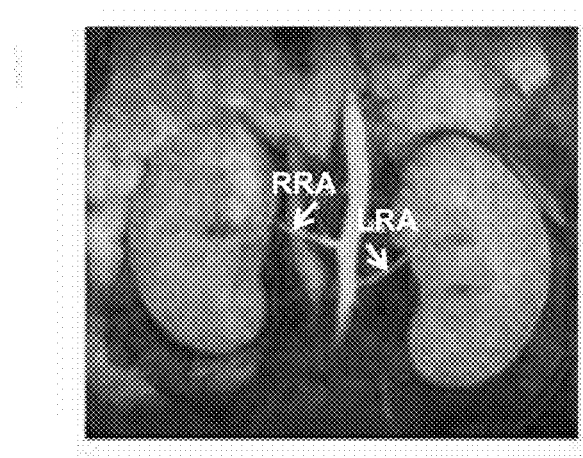
FIG. 6D refers to 3D-SPGR and shows bilateral renal artery after 20 min intravenous administration of compound 1. RRA=right renal artery; LRA=left renal artery.
Figure 6E:
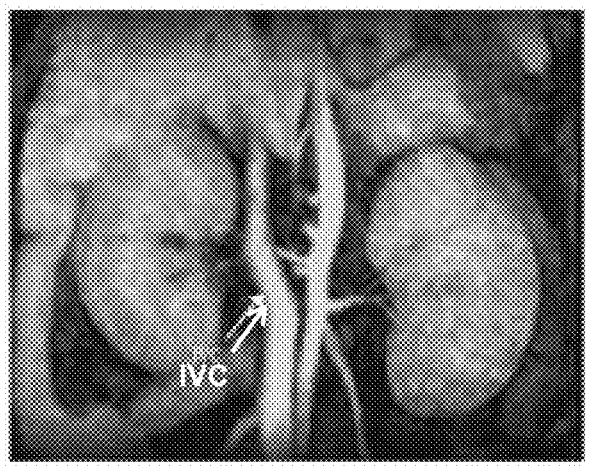
FIG. 6E refers to 3D-SPGR and shows inferior vena cava (IVC) after 40 min intravenous administration of compound 1.
Figure 11A:
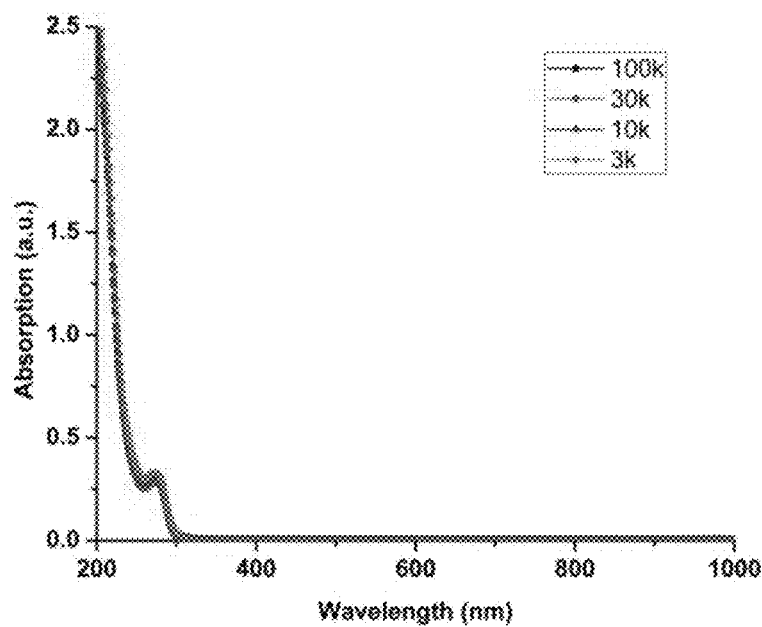
FIG. 11A shows an UV-VIS absorption spectrum of compound 1 in D.I. water after the purification process with different molecular weight cut-off membranes (100 kDa, 30 kDa, 10 kDa, and 3 kDa).
Figure 11B:
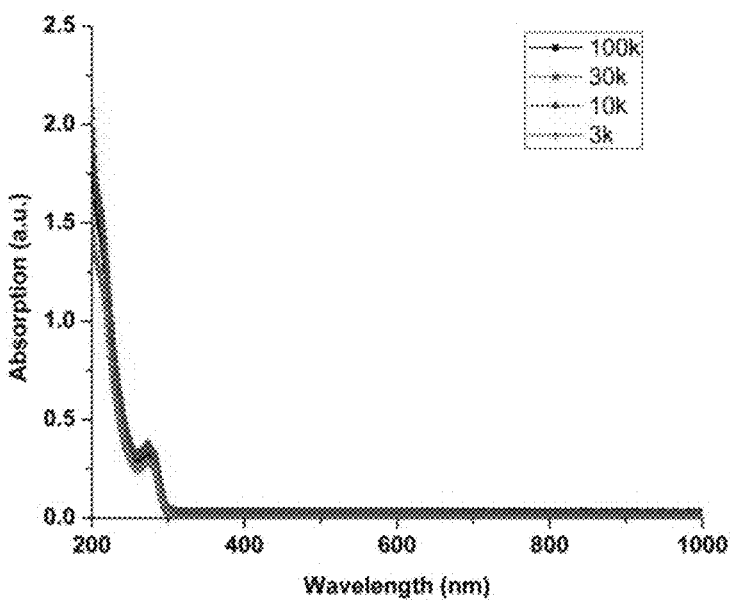
FIG. 11B shows an UV-VIS absorption spectrum of compound 2 in D.I. water after the purification process with different molecular weight cut-off membranes (100 kDa, 30 kDa, 10 kDa, and 3 kDa).
Figure 12:
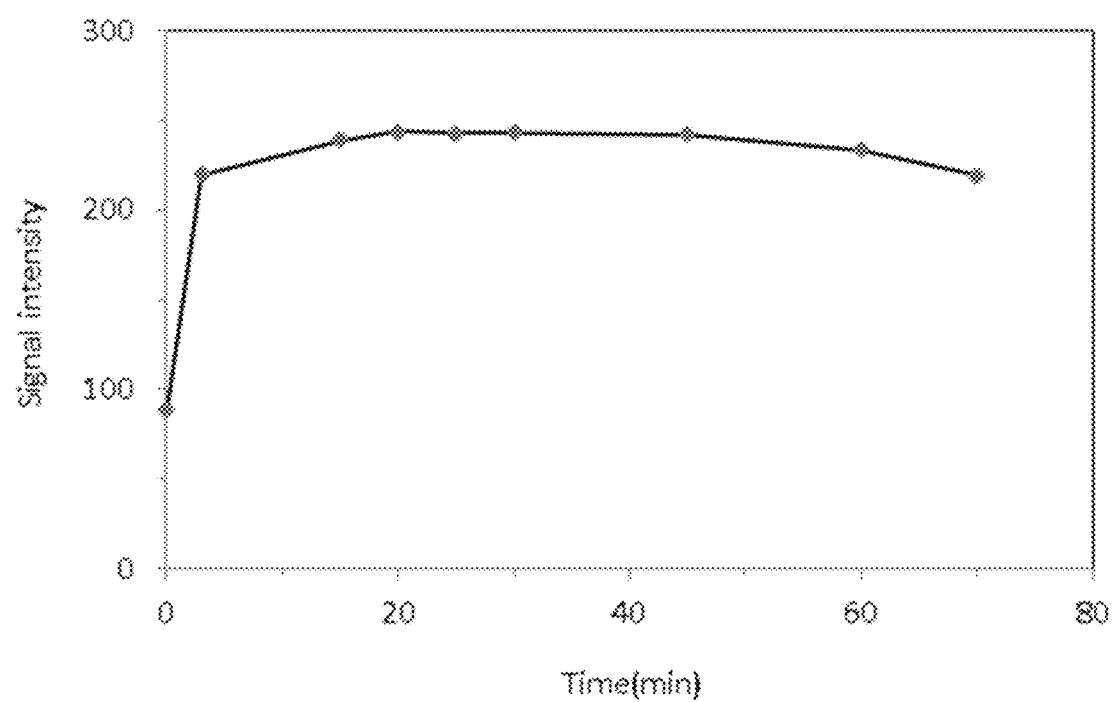
FIG. 12 shows the MR signal intensity from a dynamic study of normal kidneys after intravenous administration of compound 1.
Figure 13A:
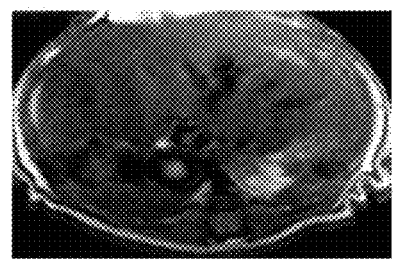
FIG. 13A shows the pre-injection image of a dynamic contrast-enhanced MR study of normal liver after intravenous administration of compound 1
Figure 13B:
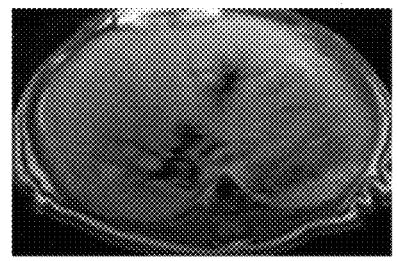
FIG. 13B shows the image of FIG. 13A, after 35 min.
Figure 13C:
FIG. 13C shows the image of FIG. 13A, after 60 min.

Compound 1 was preferably chosen for further in vivo study because in addition to its excellent water-solubility, it showed a higher $r_1$ relaxivity and lower cytotoxicity than compound 2. To validate the ability of compound 1 as a $T_1$ weighted MRI agent in living subjects, MRI of nude mice has been performed in vivo (n=4) injected via the tail vein with compound 1 (300 μL, 2.7 mg Mn/kg mice body weight, based on UV-Vis data, FIGS. 11A and 11B) using both 3.0 T and 7.0 T small animal MRI scanners. The coronal dynamic enhancement images of both kidneys and liver at different time points are shown in FIG. 6, FIG. 12 and FIG. 13A to 13C. After intravenous administration of compound 1, both kidneys showed remarkably positive signal enhancement after 15 minutes compared with the pre-injection images. The hyperintensity of both kidneys persisted about 240 minutes and then slightly attenuated in signal intensity after 24 h (FIG. 6A to 6C and FIG. 12), whereas the signal intensity of the liver was not increased obviously after 60 minutes (FIG. 13A to 13C). Such a significant change was attributed to the accumulation and secretion of the injected compound 1 in both kidneys. In comparison to conventional small molecule contrast agents, compound 1 remained within the vascular system for a prolonged period of time. Thus, compound 1 has potential as an MRI contrast agent for clinical use, especially in displaying the anatomy and pathology of the kidney. In addition, after intravenous administration, the utility of three-dimensional spoiled gradient recalled acquisition in steady state (3D-SPGR) imaging of kidneys provided bilateral renal artery images with superior sensitivity and diagnostic accuracy (FIG. 6D to 6E).

Example 5

In Vivo Toxicity Analysis and Biodistribution

In vivo toxicity was evaluated on healthy, young, non-pregnant and nulliparous Kunming mice (20~22 g). The animals were placed in clean polypropylene cages with feeding access. These cages were maintained in an air-conditioned animal house at 20±2° C., 50-70% relative humidity and 12 h light/dark cycle. The animals were provided with commercial mice pellet diet. All the animal procedures were conducted in compliance with the institutional ethics committee regulations and guidelines on animal welfare. After one week of acclimation, the mice were randomly divided into 4 groups, including one control group and three experimental groups with compounds 1 and 2 or Gd-DTPA. Each group consists of five females and five males, and was kept separately in polypropylene cages. Doses of 125 μM, 250 μM, 500 μM of compounds 1 and 2 or Gd-DTPA were dissolved in deionized water. 100 μL of each solution were intravenously injected through tail vein. One week later, the animals were sacrificed, and their heart, liver and kidneys were dissected out, stained with hematoxylin-eosin and examined under light microscopy.

The Mn elemental analysis was performed using inductively coupled plasma mass spectrometer (ICP-MS, Thermo Scientific Xseries 2 Quadrupole). Tissues were harvested from mice (3 mice each group) for biodistribution at 1 h and 24 h after intravenous injection to quantitatively assess the biodistribution of compound 1 within various organs. The organs (no more than 500 mg) were digested in a microwave (CEM MarsXpress Microwave Digester with Teflon microwave-safe vessels) before ICP analysis The samples were suspended in freshly prepared aqua regia [trace metal grade 70% nitric acid $HNO_3$/36% hydrochloric acid HCl (Fisher Scientific), 1:3 v/v] and heated until completely dissolved, and then diluted up to 8 mL with double-distilled water. The distribution of normal tissue and organs was expressed as a percentage of the injected dose per gram of tissue (% ID/g).

Figure 7A:
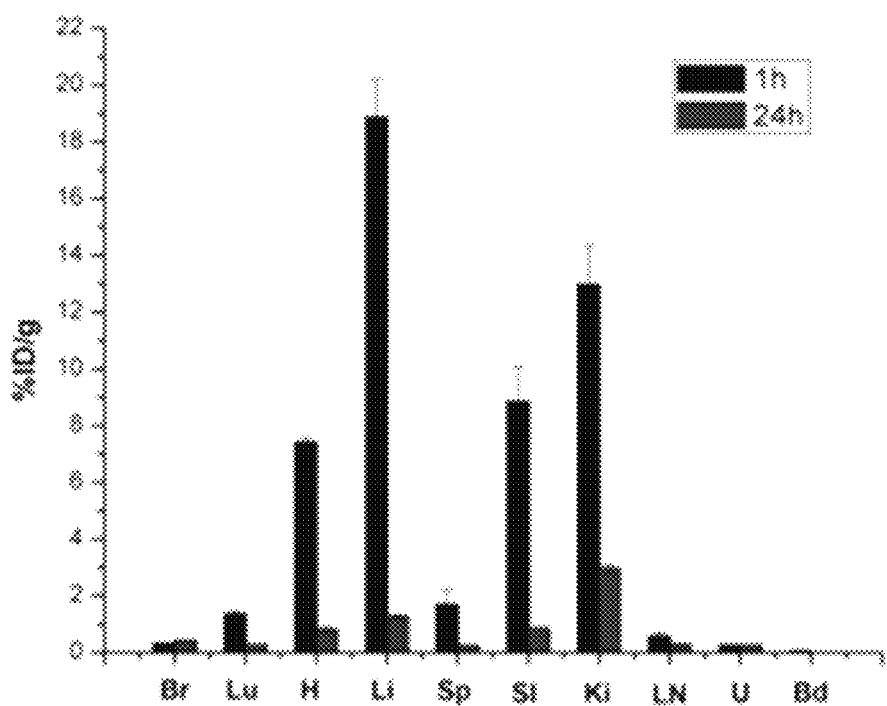
FIG. 7A refers to the biodistribution and in vivo toxicity of compounds 1 and 2 by providing a diagram showing the ICP-MS quantification analysis of compound 1 in major organs and tissues (Br, Brain; Lu, Lung; H, Heart; Li, Liver; Sp, spleen; SI, Small intestine; Ki, Kidney; LN, Lymph Node; U, Urine; Bd, Blood) at 1 h and 24 h post-injection of compound 1.

The biodistribution profiles of compound 1, obtained from the ICP-MS quantitative analysis, are presented in FIG. 7A. Compound 1 displayed a significantly high level of accumulation in liver and kidney (18.9±1.3% ID/g, 13.0±1.4% ID/g), moderate in intestine and heart (8.9±1.2% ID/g, 7.4±0.1% ID/g) and low level in lung and spleen (1.4±0.1% ID/g, 1.7±0.5% ID/g). Lowest levels were observed in brain, blood and urine (0.3±0.01% ID/g, 0.3±0.01% ID/g, and 0.1±0.03% ID/g) at 1 h after injection. At 24 h after injection, the liver (1.29±0.05% ID/g), kidney (2.97±0.16% ID/g), spleen and intestine reached very low levels.

Figure 7B:
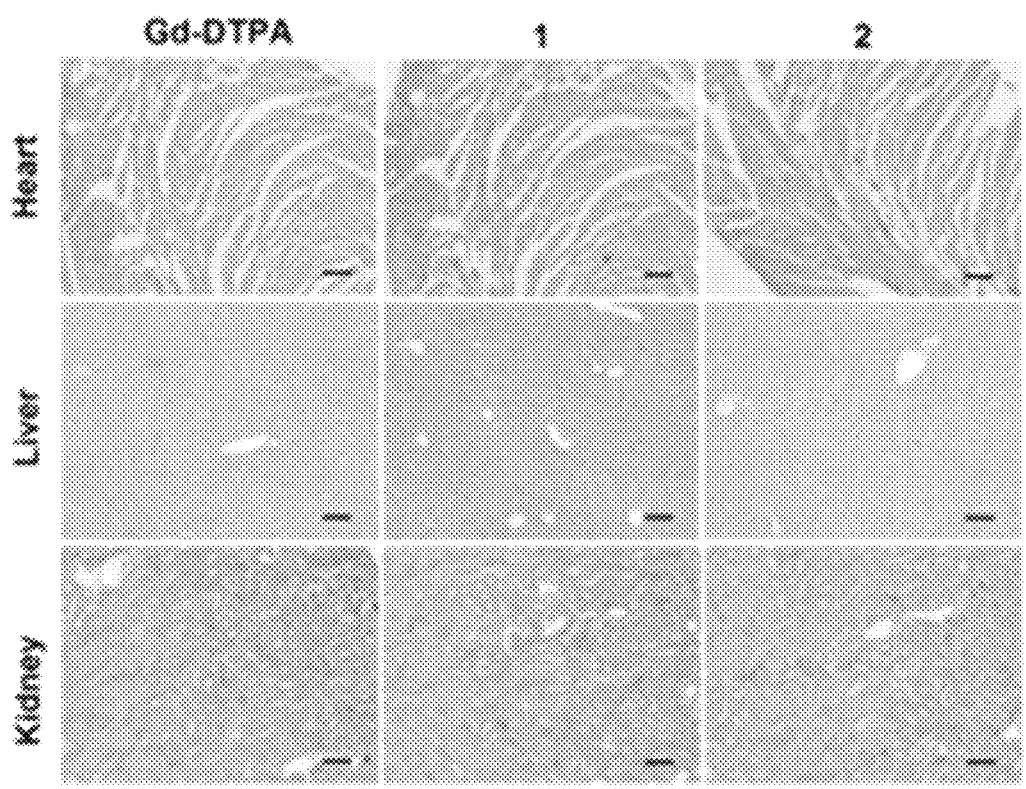
FIG. 7B shows histological morphology images of different organs of Kunming mice exposed to compounds 1 (referenced as "1") and 2 (referenced as "2") and Gd-DTPA at the concentration of 500 μM for 7 days. Scale bars show 100 μm.

In vivo analysis showed that the mice of each dose group retained shiny furs without symptoms of poisoning. None of them died within one week after administration. No change in body weights was observed between the treated and the control groups. As seen in FIG. 7B, the structures of organs from the exposed mice were normal, similar to those of the control group. Cardiac muscle tissue in the heart showed no hydropic degeneration. Hepatocytes in the liver appeared normal, and there were no inflammatory infiltrates. The glomerulus structure could be distinguished easily in the kidney. No necrosis was found in any of the groups.

The invention claimed is:
1. A method of preparing a crystalline contrast agent for magnetic resonance imaging, the method comprising steps of
(i) preparing a mixture comprising a manganese metal ion and a pyridyl ligand which pyridyl ligand is a zwitterionic pyridyl ligand having three carboxylic acid moieties;
wherein step (i) comprises steps of
a) preparing a first pre-mixture comprising steps of mixing the pyridyl ligand, a solvent and a base; and adjusting to a pH of between 5.5 and 7.5;
b) preparing a second pre-mixture comprising a step of mixing a metal salt and a solvent;
c) adding the second pre-mixture to the first pre-mixture to form a mixture; and
d) stirring the mixture obtained in step c) for between 30 min and 90 min at a temperature of between 80° C. and 120° C.;
wherein both the solvent in step a) and the solvent in step b) essentially consist of water;
(ii) subjecting the obtained mixture to conditions under which crystals of the contrast agent are formed, wherein the crystals of the contrast agent crystallize in a monoclinic space group with each asymmetric unit consisting of one dissociated water and one [$Mn_2$(Cmdcp)$_2$(H$_2$O)$_2$] coordination entity; and
(iii) separating the crystals of the contrast agent wherein the pyridyl ligand has a structure of Formula (I):

Formula (I)

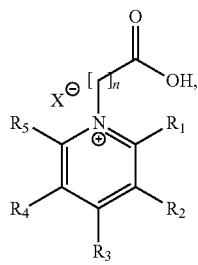

wherein X is a halogen and selected from Br, Cl, or I, n is an integer selected from 0, 1, 2, and 3, and wherein two of $R^1$ to $R^5$ are a group of Formula (II)

Formula (II)

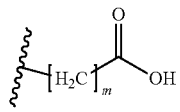

with m being an integer selected from 0, 1 and 2, and the other of $R^1$ to $R^5$ being hydrogen.

2. The method of claim 1, wherein the pyridyl ligand has a structure of Formula (III):

Formula (III)

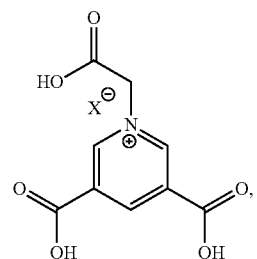

3. The method of claim 2, wherein X is Br.

4. The method of claim 1, wherein the metal salt is $MnCl_2$.

5. The method of claim 1, wherein the base is sodium hydroxide.

6. The method of claim 1, wherein step (ii) comprises steps of
   a) optionally stirring the mixture of step (i); and
   b) allowing the mixture to stand at a temperature between 20° C. and 30° C. for at least 48 hours for forming crystals of the contrast agent.

7. The method of claim 1, wherein step (iii) comprises steps of:
   a) separating the crystals from the mixture; and
   b) drying the crystals.

* * * * *